US012661246B2

(12) United States Patent
Loughnane et al.

(10) Patent No.: US 12,661,246 B2
(45) Date of Patent: Jun. 23, 2026

(54) DEVICE AND METHOD FOR COMPRESSING AND LOADING A STENT

(71) Applicant: BOSTON SCIENTIFIC SCIMED, INC., Maple Grove, MN (US)

(72) Inventors: Declan Loughnane, Galway (IE); Tim O'Connor, Galway (IE); Pearse A. Coffey, Galway (IE); Joseph Murphy, Galway (IE)

(73) Assignee: Boston Scientific Scimed, Inc., Maple Grove, MN (US)

( * ) Notice: Subject to any disclaimer, the term of this patent is extended or adjusted under 35 U.S.C. 154(b) by 922 days.

(21) Appl. No.: 17/963,560

(22) Filed: Oct. 11, 2022

(65) Prior Publication Data

US 2023/0110138 A1      Apr. 13, 2023

Related U.S. Application Data

(60) Provisional application No. 63/254,695, filed on Oct. 12, 2021.

(51) Int. Cl.
*A61F 2/844*        (2013.01)
*A61F 2/92*         (2013.01)
*A61F 2/95*         (2013.01)

(52) U.S. Cl.
CPC ................ *A61F 2/844* (2013.01); *A61F 2/92* (2013.01); *A61F 2/9522* (2020.05)

(58) Field of Classification Search
CPC .... A61F 2/844; A61F 2/92; A61F 2/95; A61F 2/9522; A61F 2/9524
See application file for complete search history.

(56) References Cited

U.S. PATENT DOCUMENTS

| | | | |
|---|---|---|---|
| 1,055,825 | A | 3/1913 | Snyder |
| 6,823,576 | B2 | 11/2004 | Austin |
| 7,578,041 | B2 | 8/2009 | Weber et al. |
| 8,011,078 | B2 | 9/2011 | Pacetti |

(Continued)

FOREIGN PATENT DOCUMENTS

| | | |
|---|---|---|
| WO | 2015179181 A1 | 11/2015 |
| WO | 2020153965 A1 | 7/2020 |

OTHER PUBLICATIONS

International Search Report and Written Opinion dated Jan. 9, 2023 for International Application No. PCT/US2022/046263.

*Primary Examiner* — William H Matthews
(74) *Attorney, Agent, or Firm* — Seager, Tufte & Wickhem LLP

(57)        ABSTRACT

A device for radially compressing a stent may include a housing including a central opening and a first iris positioned adjacent the housing. The first iris includes a first circumferential ring and a first plurality of arms extending radially inward from the first circumferential ring to define a first central opening. The device may include a second iris axially offset from the first iris and including a second circumferential ring and a second plurality of arms extending radially inward from the second circumferential ring to define a second central opening. Rotation of the circumferential ring(s) relative to the housing changes a size of their respective central opening(s). The plurality of arms may shift between a first configuration and a second configuration via rotation of the circumferential ring(s) relative to the housing.

19 Claims, 13 Drawing Sheets

(56)     References Cited

U.S. PATENT DOCUMENTS

|  |  |  |  |  |
|---|---|---|---|---|
| 8,221,824 | B2 | 7/2012 | Timm | |
| 8,291,570 | B2 | 10/2012 | Eidenschink et al. | |
| 8,333,000 | B2 | 12/2012 | Huang et al. | |
| 8,474,122 | B2 | 7/2013 | Melsheimer | |
| 8,544,160 | B2 | 10/2013 | Kokish et al. | |
| 8,595,913 | B2 | 12/2013 | Knott et al. | |
| 8,632,847 | B2 | 1/2014 | Pacetti | |
| 8,752,261 | B2 | 6/2014 | Van Sciver | |
| 9,125,763 | B2 | 9/2015 | Wang et al. | |
| 9,138,338 | B2 | 9/2015 | Chambers et al. | |
| 9,895,241 | B2 | 2/2018 | Wang | |
| 10,292,844 | B2 | 5/2019 | Orth et al. | |
| 10,307,277 | B2 | 6/2019 | Wang | |
| 10,357,363 | B2 | 7/2019 | Frisby | |
| 10,660,773 | B2 | 5/2020 | Wang et al. | |
| 10,918,478 | B2 | 2/2021 | Taft et al. | |
| 10,967,556 | B2 | 4/2021 | Wang et al. | |
| 2008/0053182 | A1* | 3/2008 | Goff ......................... | A61F 2/95 |
| | | | | 72/367.1 |
| 2016/0199184 | A1* | 7/2016 | Ma ........................ | B21D 11/08 |
| | | | | 623/2.11 |
| 2019/0183642 | A1 | 6/2019 | Tegels et al. | |

* cited by examiner

DEVICE AND METHOD FOR COMPRESSING AND LOADING A STENT

CROSS-REFERENCE TO RELATED APPLICATIONS

This application claims the benefit of priority of U.S. Provisional Application No. 63/254,695 filed Oct. 12, 2021, the entire disclosure of which is hereby incorporated by reference.

TECHNICAL FIELD

The present disclosure pertains to medical devices, systems, and methods for manufacturing and/or using medical devices and/or systems. More particularly, the present disclosure pertains to a device and/or method for radially compressing and/or loading a stent and/or a stent device such as a replacement heart valve implant.

BACKGROUND

Conventional stent crimping devices have been used throughout the medical device industry to crimp balloon expandable stents, self-expanding stents, replacement heart valve implants, etc. Conventional stent crimping devices have complex arrangements of multiple parts and/or difficult assemblies and rely upon complex interactions between many moving parts. The cost of a conventional stent crimping device may be significant due to the aforementioned complexity and number of components required and/or used in a conventional stent crimping device. Of the known devices and methods for compressing and/or crimping stents, each has certain advantages and disadvantages. There is an ongoing need for alternative devices and/or methods for compressing stents, stent devices, and/or other medical implants that may include a stent, such as but not limited to replacement heart valve implants.

SUMMARY

In one example, a device for radially compressing a stent may comprise a housing including a central opening, and a first iris positioned adjacent the housing. The first iris includes a first circumferential ring positioned coaxially relative to the central opening and a first plurality of arms extending radially inward from the first circumferential ring. The first plurality of arms defines a first central opening positioned coaxially relative to the central opening of the housing. Rotation of the first circumferential ring relative to the housing changes a size of the first central opening.

In addition or alternatively to any example described herein, a first end of each arm of the first plurality of arms is connected to the first circumferential ring by a first living hinge disposed between the first end and the first circumferential ring.

In addition or alternatively to any example described herein, a second end of each arm of the first plurality of arms is secured relative to the housing.

In addition or alternatively to any example described herein, the second end of each arm of the first plurality of arms includes an aperture formed therein.

In addition or alternatively to any example described herein, a fastener extends through the aperture and engages with the housing.

In addition or alternatively to any example described herein, the aperture is configured to engage with a protrusion extending from the housing.

In addition or alternatively to any example described herein, a medial portion of each arm of the first plurality of arms is configured to engage with medial portions of circumferentially adjacent arms of the first plurality of arms to define the first central opening.

In addition or alternatively to any example described herein, the medial portion of each arm includes a second living hinge.

In addition or alternatively to any example described herein, the first plurality of arms is monolithically formed with the first circumferential ring from a single piece of material.

In addition or alternatively to any example described herein, and in another example, a device for radially compressing a stent may comprise a housing including a central opening, and a first iris positioned adjacent the housing. The first iris includes a first circumferential ring positioned coaxially relative to the central opening of the housing and a first plurality of arms extending radially inward from the first circumferential ring. The first plurality of arms defines a first central opening positioned coaxially relative to the central opening of the housing. The first plurality of arms is configured to shift between a first configuration and a second configuration via rotation of the first circumferential ring relative to the housing.

In addition or alternatively to any example described herein, in the first configuration, the first plurality of arms defines a first size of the first central opening, and in the second configuration, the first plurality of arms defines a second size of the first central opening less than the first size.

In addition or alternatively to any example described herein, each arm of the first plurality of arms engages at least one other arm of the first plurality of arms as the first plurality of arms shifts from the first configuration to the second configuration.

In addition or alternatively to any example described herein, a first end of each arm of the first plurality of arms is fixedly attached to the first circumferential ring by a first living hinge.

In addition or alternatively to any example described herein, the device may comprise a second iris axially offset from the first iris. The second iris includes a second circumferential ring positioned coaxially relative to the central opening of the housing and a second plurality of arms extending radially inward from the second circumferential ring. The second plurality of arms defines a second central opening positioned coaxially relative to the central opening of the housing. The second plurality of arms is configured to shift between a first configuration and a second configuration via rotation of the second circumferential ring relative to the housing.

In addition or alternatively to any example described herein, and in another example, a method of radially compressing a stent may comprise inserting a stent in a first configuration into a first iris, wherein the first iris includes a first circumferential ring and a first plurality of arms extending radially inward from the first circumferential ring to define a first central opening; and rotating the first circumferential ring relative to a housing disposed about the first circumferential ring to shift the first plurality of arms from a first configuration to a second configuration, wherein the first central opening has a first size in the first configuration and a second size in the second configuration less than the first size. In the second configuration of the first plurality of arms, a first portion of the stent disposed within the first iris is in a radially compressed configuration.

In addition or alternatively to any example described herein, the method may comprise positioning a sheath proximate the first iris with the first plurality of arms in the second configuration and the first portion of the stent disposed within the first iris in the radially compressed configuration; rotating the first circumferential ring relative to the housing to shift the first plurality of arms from the second configuration to the first configuration; and moving the sheath into the first iris over the stent such that the first portion of the stent that was disposed within the first iris is disposed within the sheath.

In addition or alternatively to any example described herein, the sheath has an inner diameter less than an outer diameter of the stent in the first configuration.

In addition or alternatively to any example described herein, inserting the stent further includes inserting the stent in the first configuration into the first iris and a second iris axially offset from the first iris, wherein the second iris includes a second circumferential ring and a second plurality of arms extending radially inward from the second circumferential ring to define a second central opening.

In addition or alternatively to any example described herein, the method may comprise rotating the second circumferential ring relative to the housing to shift the second plurality of arms from a first configuration to a second configuration, wherein the second central opening has a first size in the first configuration and a second size in the second configuration less than the first size. In the second configuration of the second plurality of arms, a second portion of the stent disposed within the second iris is in the radially compressed configuration.

In addition or alternatively to any example described herein, the method may comprise positioning a sheath proximate the first iris with the first plurality of arms in the second configuration and the first portion of the stent disposed within the first iris in the radially compressed configuration; rotating the first circumferential ring relative to the housing to shift the first plurality of arms from the second configuration to the first configuration; moving the sheath into the first iris over the stent such that the first portion of the stent that was disposed within the first iris is disposed within the sheath; rotating the second circumferential ring relative to the housing to shift the second plurality of arms from the second configuration to the first configuration; and moving the sheath into the second iris over the stent such that the second portion of the stent that was disposed within the second iris is disposed within the sheath.

The above summary of some embodiments, aspects, and/or examples is not intended to describe each disclosed embodiment or every implementation of the present disclosure. The figures and detailed description which follow more particularly exemplify these embodiments.

BRIEF DESCRIPTION OF THE DRAWINGS

The disclosure may be more completely understood in consideration of the following detailed description in connection with the accompanying drawings, in which.

Figure 1:
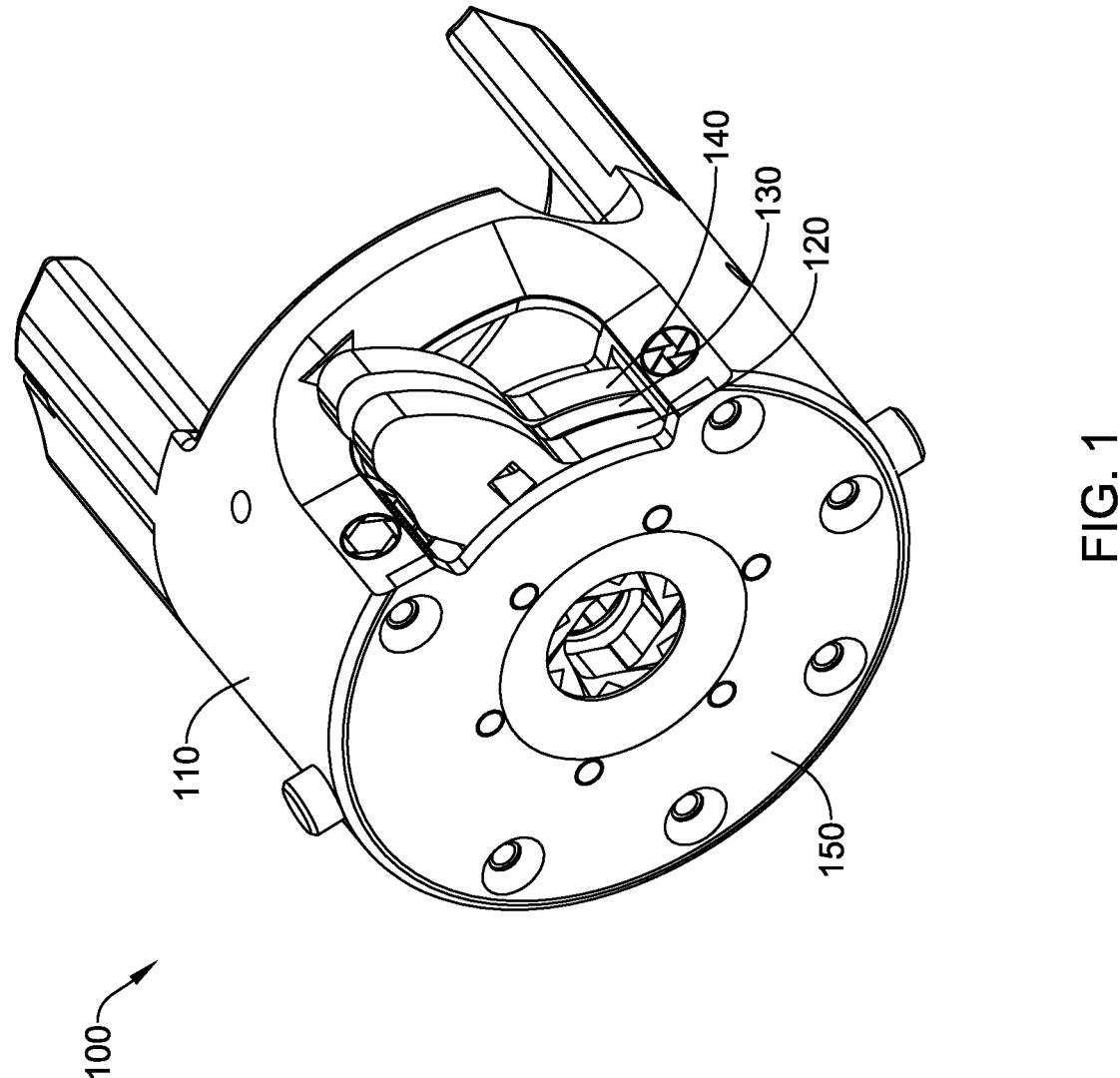
FIGS. 1-2 illustrates selected aspects of a device for radially compressing a stent.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate example embodiments of the disclosure but not limit the disclosure. Those skilled in the art will recognize that the various elements described and/or shown may be arranged in various combinations and configurations without departing from the scope of the disclosure. However, in the interest of clarity and ease of understanding, every feature and/or element may not be shown in each drawing.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Still other relative terms, such as "axial", "circumferential", "longitudinal", "lateral", "radial", etc. and/or variants thereof generally refer to direction and/or orientation relative to a central longitudinal axis of the disclosed structure or device.

The term "extent" may be understood to mean the greatest measurement of a stated or identified dimension, unless the extent or dimension in question is preceded by or identified as a "minimum", which may be understood to mean the smallest measurement of the stated or identified dimension. For example, "outer extent" may be understood to mean an outer dimension, "radial extent" may be understood to mean a radial dimension, "longitudinal extent" may be understood to mean a longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered the greatest possible dimension measured according to the intended usage, while a "minimum extent" may be considered the smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete structures or elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to use the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For example, a reference to "the arm", "the aperture", or other features may be equally referred to all instances and quantities beyond one of said feature unless clearly stated to the contrary. As such, it will be understood that the following discussion may apply equally to any and/or all of the components for which there are more than one within the device, etc. unless explicitly stated to the contrary.

Additionally, it should be noted that in any given figure, some features may not be shown, or may be shown schematically, for clarity and/or simplicity. Additional details regarding some components and/or method steps may be illustrated in other figures in greater detail. The devices and/or methods disclosed herein may provide a number of desirable features and benefits as described in more detail below. For the purpose of this disclosure, the discussion below is directed toward a device and method for radially compressing a stent and will be so described in the interest of brevity. This, however, is not intended to be limiting as the skilled person will recognize that the following discussion may also apply to stent devices or medical implants including a stent with no or minimal changes to the structure and/or scope of the disclosure. Similarly, the devices and methods disclosed herein may have applications and uses for other medical devices.

Figure 2:
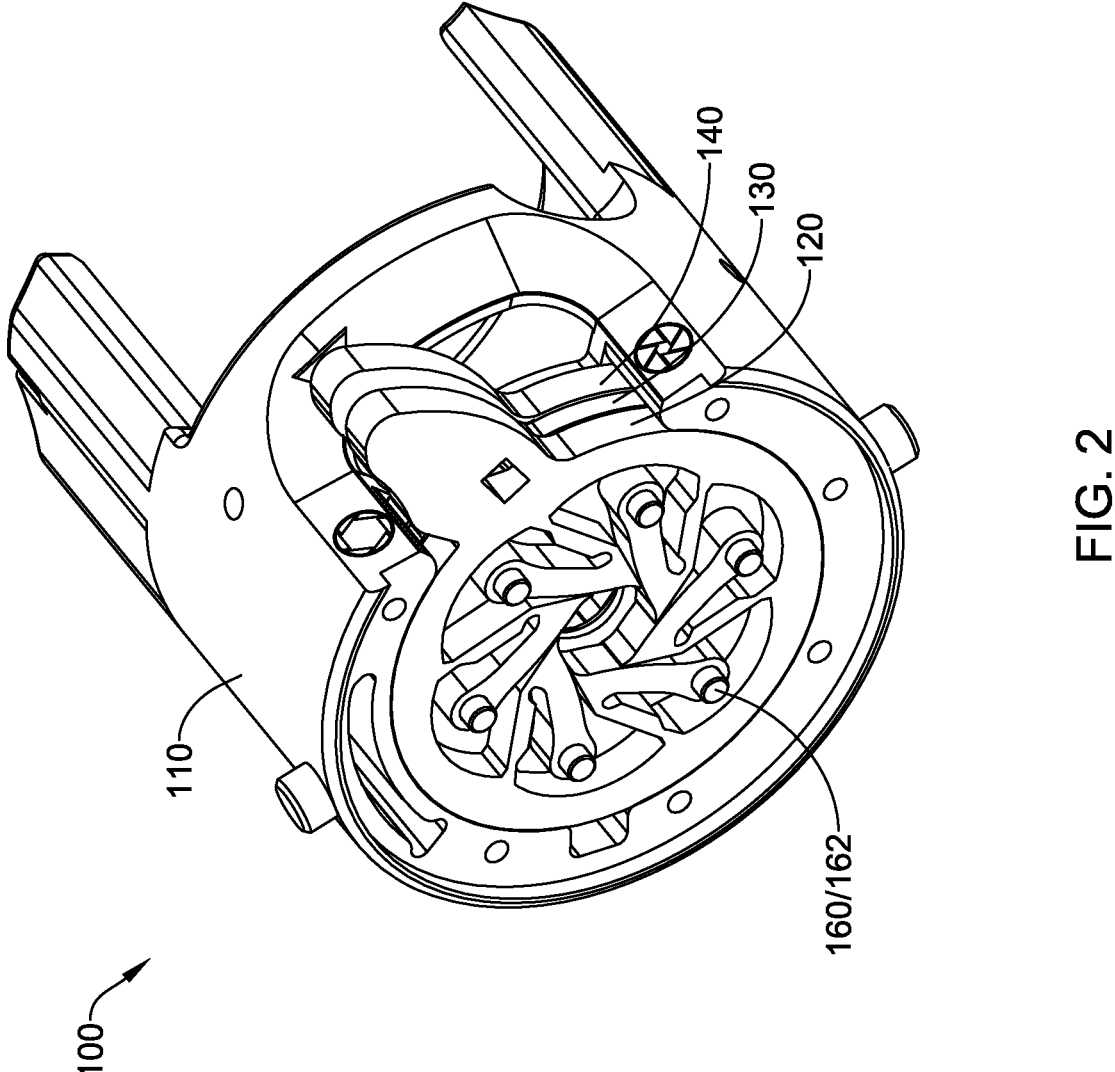
Figure 3:
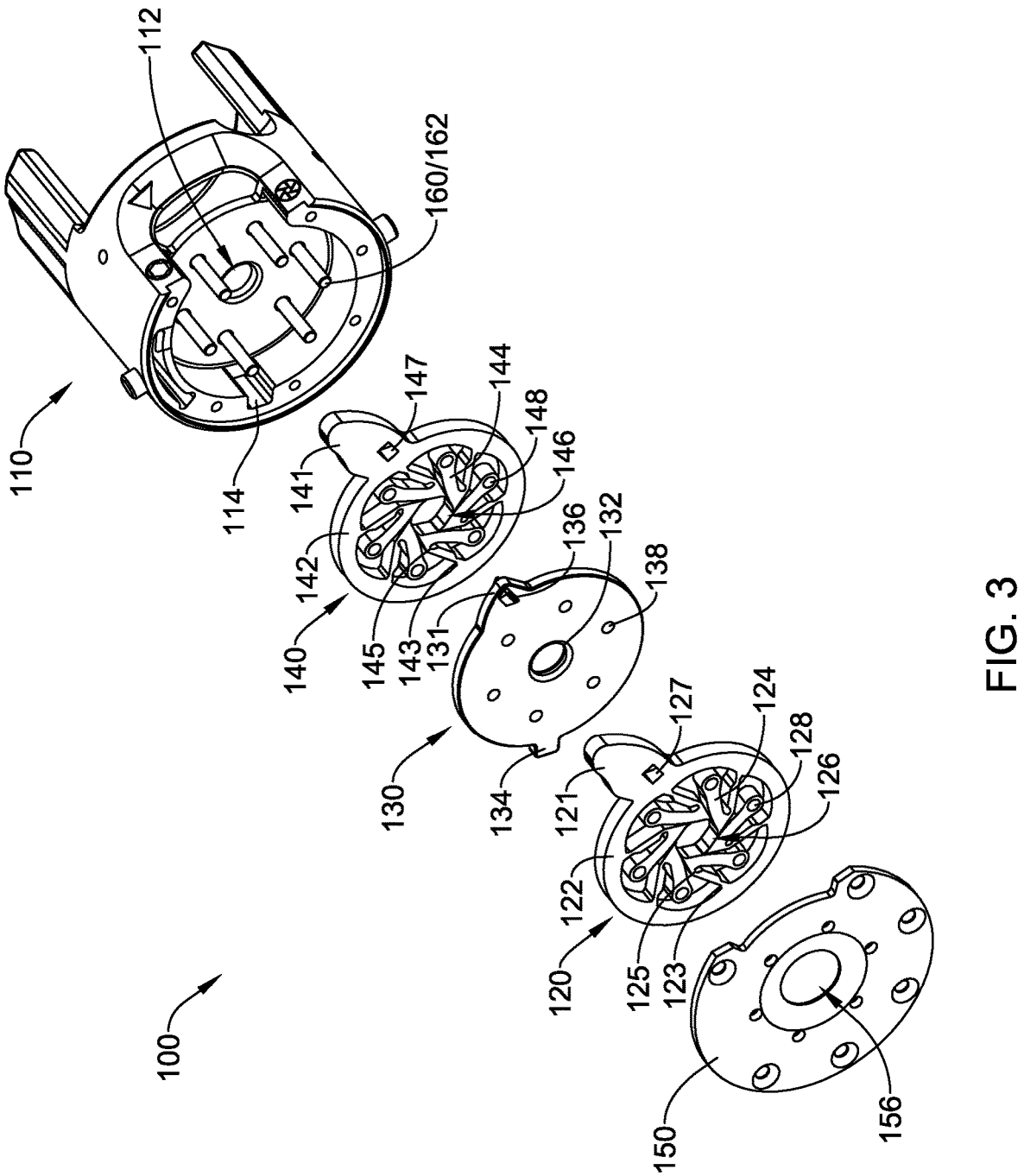
FIG. 3 is an exploded view illustrating selected aspects of the device of FIGS. 1-2.

FIGS. 1-3 illustrate aspects of a device 100 for radially compressing a stent. The device 100 may include a housing 110 including a central opening 112 (e.g., FIG. 3). In some embodiments, the device 100 may include a first iris 120 positioned adjacent the housing 110. In at least some embodiments, the first iris 120 may be positioned at least partially within the housing 110. In some embodiments, the device 100 may include a spacer plate 130 positioned adjacent the housing 110. In at least some embodiments, the spacer plate 130 may be positioned at least partially within the housing 110. In some embodiments, the device 100 may include a second iris 140 positioned adjacent the housing 110. In at least some embodiments, the second iris 140 may be positioned at least partially within the housing 110. In some embodiments, the device 100 may include a cover plate 150 positioned adjacent the housing 110. In some embodiments, the cover plate 150 may be positioned at least partially within the housing 110.

In some embodiments, the spacer plate 130 may be non-rotatable relative to the housing 110. In some embodiments, the spacer plate 130 may engage the housing 110 as discussed herein to prevent relative rotation therebetween. In some embodiments, the cover plate 150 may be removably secured to the housing 110. In some embodiments, the cover plate 150 may be non-rotatable relative to the housing 110. In one example, the cover plate 150 may be removably secured to the housing 110 using one or more fasteners (not shown). In another example, the cover plate 150 and/or one or more protrusions extending from the cover plate 150 may be configured to engage one or more slots or other features formed in the housing 110 to removably secure the cover plate 150 to the housing 110. Other configurations are also contemplated.

In some embodiments, the first iris 120 may be movable with respect to the housing 110, the spacer plate 130, and/or the cover plate 150. In some embodiments, at least a portion of the first iris 120 may be configured to rotate relative to the housing 110, the spacer plate 130, and/or the cover plate 150.

In some embodiments, the second iris 140 may be movable with respect to the housing 110, the spacer plate 130, and/or the cover plate 150. In some embodiments, at least a portion of the second iris 140 may be configured to rotate relative to the housing 110, the spacer plate 130, and/or the cover plate 150. In some embodiments, at least a portion of the second iris 140 may be configured to rotate relative to the first iris 120. Accordingly, in at least some embodiments, the first iris 120 and the second iris 140 may be movable independently of each other. In some embodiments, the first iris 120 may be movable and/or may be configured to rotate relative to the housing 110, the spacer plate 130, and/or the cover plate 150 independently of the second iris 140. In some embodiments, the second iris 140 may be movable and/or may be configured to rotate relative to the housing 110, the spacer plate 130, and/or the cover plate 150 independently of the first iris 120.

In some embodiments, the first iris 120 and the second iris 140 may be movable and/or may be configured to rotate relative to the housing 110, the spacer plate 130, and/or the cover plate 150 together, in tandem, and/or simultaneously. In some embodiments, the first iris 120 and the second iris 140 may be movable and/or may be configured to rotate relative to the housing 110, the spacer plate 130, and/or the cover plate 150 together, in tandem, and/or simultaneously at one time, in one direction, or during a particular step of a method disclosed herein, and the first iris 120 and the second iris 140 may be movable and/or may be configured to rotate relative to the housing 110, the spacer plate 130, and/or the cover plate 150 independently of each other at another time, in another direction, or during another particular step of a method disclosed herein. Other configurations are also contemplated.

FIG. 2 illustrates selected aspects of the device 100 with the cover plate 150 removed. In some embodiments, the device 100 may include a fastener 160 engaged with the housing 110. In some embodiments, the fastener 160 may be removable from and/or configured to be disengaged from the housing 110. The fastener 160 may be configured to engage the first iris 120, the spacer plate 130, the second iris 140, and/or the cover plate 150. In some embodiments, the device 100 may include a plurality of fasteners 160 engaged with the housing 110. In some embodiments, the plurality of fasteners 160 may be removable from and/or configured to be disengaged from the housing 110. Other configurations are also contemplated.

In some embodiments, the device 100 may include a protrusion 162 extending from the housing 110. In some embodiments, the protrusion 162 may be fixedly attached to the housing 110. In some embodiments, the protrusion 162 may be removable from and/or configured to be disengaged from the housing 110. The protrusion 162 may be configured to engage the first iris 120, the spacer plate 130, the second iris 140, and/or the cover plate 150. In some embodiments, the device 100 may include a plurality of protrusions 162 extending from the housing 110. In some embodiments, the plurality of protrusions 162 may be fixedly attached to the housing 110. In some embodiments, the plurality of protrusions 162 may be removable from and/or configured to be disengaged from the housing 110. Other configurations are also contemplated.

FIG. 3 is an exploded view illustrating selected aspects of the device 100. As discussed above, the housing 110 may include the central opening 112 formed therein. In some embodiments, the cover plate 150 may include a cover plate opening 156. The cover plate opening 156 may be aligned with and/or may be positioned coaxially relative to the central opening 112 of the housing 110. In some embodiments, the cover plate 150 may include a plurality of openings extending along a perimeter of the cover plate 150. The plurality of openings may be configured to receive fasteners therein to removably secure and/or attach the cover plate 150 to the housing 110. The housing 110 may include a plurality of corresponding holes or recesses aligned with the plurality of openings in the cover plate 150 and configured to receive the fasteners therein. In one example, the fasteners may be externally threaded screws or other threaded fasteners and the plurality of corresponding holes or recessed may include internal threads configured to threadably engage the externally threaded screws or other threaded fasteners. Other configurations and/or fastener types are also contemplated. Some suitable but non-limiting examples of materials that may be used to for the housing 110 and/or the cover plate 150, including but not limited to metals and metal alloys, composites, ceramics, polymers, and the like, are described below.

In some embodiments, the first iris 120 may include a first circumferential ring 122 positioned coaxially relative to the central opening 112 of the housing 110. In some embodiments, the first circumferential ring 122 may be positioned adjacent the housing 110. In some embodiments, the first circumferential ring 122 may be positioned at least partially within the housing 110. In some embodiments, the first iris 120 and/or the first circumferential ring 122 may have a substantially circular outer perimeter.

The first iris 120 may include a first plurality of arms 124 extending radially inward from the first circumferential ring 122. The first plurality of arms 124 may define a first central opening 126 of the first iris 120. The first central opening 126 may be aligned with and/or may be positioned coaxially relative to the central opening 112 of the housing 110. Some aspects of the first iris 120 and/or elements thereof are shown in greater detail in FIG. 4.

A first end of each arm of the first plurality of arms 124 may be connected to the first circumferential ring 122 by a first living hinge 123 disposed between the first end and the first circumferential ring 122. In some embodiments, the first end of each arm of the first plurality of arms 124 may be directly connected to the first circumferential ring 122 by the first living hinge 123. In some embodiments, the first end of each arm of the first plurality of arms 124 may be fixedly attached to the first circumferential ring 122 by the first living hinge 123. In some embodiments, a second end of each arm of the first plurality of arms 124 may be secured relative to the housing 110. In some embodiments, the second end of each arm of the first plurality of arms 124 may include an aperture 128 formed therein. In some embodiments, the fastener 160 extends through the aperture 128 and engages with the housing 110. In some embodiments, the aperture 128 may be configured to engage with the protrusion 162 extending from the housing 110. In at least some embodiments, the second end of each of the first plurality of arms 124 may be configured to rotate about the fastener 160 and/or the protrusion 162 when the first circumferential ring 122 is rotated relative to the housing 110.

Figure 4:
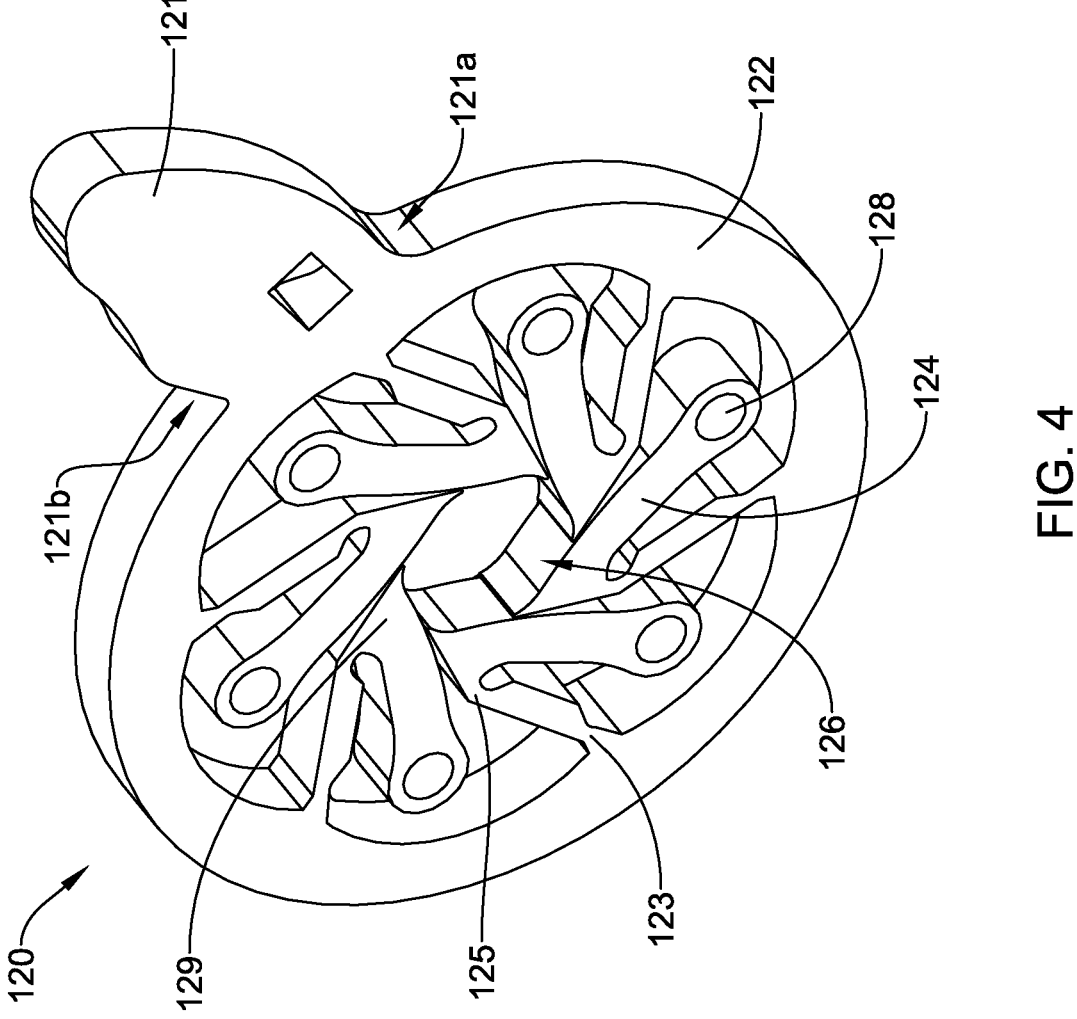
FIG. 4 illustrates selected aspects of a first iris of the device of FIGS. 1-3.

As shown in FIG. 4, a medial portion 129 of each arm of the first plurality of arms 124 may be configured to engage with medial portions of circumferentially adjacent arms of the first plurality of arms 124 to define the first central opening 126. The medial portion 129 of each arm of the first plurality of arms 124 may include a second living hinge 125. In some embodiments, the first plurality of arms 124 may be integrally and/or monolithically formed with the first circumferential ring 122 from a single piece of material. In at least some embodiments, the first living hinge 123 and the second living hinge 125 of each arm of the first plurality of arms 124 may be configured to resiliently flex, deflect, and/or bend to permit relative movement between portions of each arm on opposite sides of the first living hinge 123 and/or the second living hinge 125. Some suitable but non-limiting examples of materials that may be used to form the first iris 120, the first circumferential ring 122, the first plurality of arms 124, etc., including but not limited to metals and metal alloys, composites, ceramics, polymers, and the like, are described below.

In some embodiments, the first iris 120 may be manufactured using one or more a variety of methods. In some embodiments, the first iris 120 may be machined. In some embodiments, the first iris 120 may be cut using a waterjet. In some embodiments, the first iris 120 may be laser cut. In some embodiments, the first iris 120 may be injection molded. In some embodiments, the first iris 120 may be cast. Other methods of manufacture are also contemplated.

In some embodiments, the first iris 120 may include a first lever 121 fixedly attached to and/or extending radially outward from the first circumferential ring 122. In some embodiments, the first lever 121 may extend radially outward from the substantially circular outer perimeter of the first iris 120 and/or the first circumferential ring 122. In at least some embodiments, the first lever 121 may include a first cavity 127 formed therein. The first lever 121 may extend radially outward along a first radii extending outward from a center of the first central opening 126. Additionally, the first lever 121 may include a first side surface 121A facing laterally from the first radii in a first direction and a second side surface 121B disposed generally opposite the first side surface 121A, the second side surface 121B facing laterally from the first radii in a second direction generally opposite the first direction. In at least some embodiments, the first cavity 127 may be disposed between the first side surface 121A and the second side surface 121B of the first lever 121. In some embodiments, the first cavity 127 may be disposed radially between the first side surface 121A and the second side surface 121B of the first lever 121. In some embodiments, the first cavity 127 may be directly radially between the first side surface 121A and the second side surface 121B of the first lever 121. The purpose and/or use of the first side surface 121A and/or the second side surface 121B of the first lever 121 will be apparent.

Returning to FIG. 3, in some embodiments, the device 100 may include the spacer plate 130. In some embodiments, the spacer plate 130 may include a central opening 132 formed therein. In some embodiments, the central opening 132 of the spacer plate 130 may be aligned with and/or may be positioned coaxially relative to the central opening 112 of the housing 110 and/or the first central opening 126 of the first iris 120. In some embodiments, the spacer plate 130 may be disposed axially between the first iris 120 and the housing 110 with respect to an axis extending through the central opening 112 of the housing 110 and the first central opening 126 of the first iris 120. In some embodiments, the spacer plate 130 may be configured slide axially into the housing 110. The housing 110 may include a notch or a recess 114 formed in a sidewall of the housing 110. The spacer plate 130 may include a locking tab 134 projecting radially outward from the spacer plate 130. The locking tab 134 may be configured to engage with the recess 114 of the housing 110 to prevent relative rotation between the spacer plate 130 and the housing 110. In some embodiments, the spacer plate 130 may include a plurality of holes 138 formed therein, wherein the plurality of holes 138 is configured to receive and/or engage with the fastener 160 and/or the protrusion 162.

In some embodiments, the spacer plate 130 may have a substantially circular outer perimeter. In at least some embodiments, the spacer plate 130 may include a projection 131 extending radially outward from the spacer plate 130. In some embodiments, the projection 131 may extend radially outward from the substantially circular outer perimeter of the spacer plate 130. In some embodiments, the projection 131 may include a first stop element 136 projecting axially and/or upward from an upper surface of the projection 131 and/or the spacer plate 130. In some embodiments, the first stop element 136 may be configured to engage and/or be received by the first cavity 127 of the first lever 121 of the first iris 120 to lock the first iris 120 and/or the first plurality of arms 124 in a first configuration. In at least some embodiments, the first configuration of the first iris 120 and/or the first plurality of arms 124 may be an open configuration or a radially expanded configuration. In the first configuration of the first iris 120 and/or the first plurality of arms 124, the first plurality of arms 124 and/or the medial portion 129 of each arm of the first plurality of arms 124 may define a first size of the first central opening 126.

In some embodiments, the device 100 may be devoid of the spacer plate 130. In some embodiments, the first iris 120 may be positioned immediately adjacent to an upward facing surface of the housing 110 defining the central opening 112. Such a configuration may be useful for radially compressing a relative short and/or limited length stent, or where only a portion of the stent needs to be radially compressed.

In some embodiments, the device 100 may include the second iris 140. The second iris 140 may be axially offset from the first iris 120. In some embodiments, the second iris 140 may be spaced apart from the first iris 120. In some embodiments, the second iris 140 may be spaced apart from the first iris 120 by the spacer plate 130. In some embodiments, the second iris 140 may include a second circumferential ring 142 positioned coaxially relative to the central opening 112 of the housing 110. In some embodiments, the second circumferential ring 142 may be positioned adjacent the housing 110. In some embodiments, the second circumferential ring 142 may be positioned at least partially within the housing 110. In some embodiments, the second iris 140 and/or the second circumferential ring 142 may have a substantially circular outer perimeter.

The second iris 140 may include a second plurality of arms 144 extending radially inward from the second circumferential ring 142. The second plurality of arms 144 may define a second central opening 146 of the second iris 140. The second central opening 146 may be aligned with and/or may be positioned coaxially relative to the central opening 112 of the housing 110, the central opening 132 of the spacer plate 130, and/or the first central opening 126 of the first iris 120. Some aspects of the second iris 140 and/or elements thereof may be substantially the same as or similar to elements of the first iris 120 shown in FIG. 4.

A first end of each arm of the second plurality of arms 144 may be connected to the second circumferential ring 142 by a first living hinge 143 disposed between the first end and the second circumferential ring 142. In some embodiments, the first end of each arm of the second plurality of arms 144 may be directly connected to the second circumferential ring 142 by the first living hinge 143. In some embodiments, the first end of each arm of the second plurality of arms 144 may be fixedly attached to the second circumferential ring 142 by the first living hinge 143. In some embodiments, a second end of each arm of the second plurality of arms 144 may be secured relative to the housing 110. In some embodiments, the second end of each arm of the second plurality of arms 144 may include an aperture 148 formed therein. In some embodiments, the fastener 160 extends through the aperture 148 and engages with the housing 110. In some embodiments, the aperture 148 may be configured to engage with the protrusion 162 extending from the housing 110. In at least some embodiments, the second end of each of the second plurality of arms 144 may be configured to rotate about the fastener 160 and/or the protrusion 162 when the second circumferential ring 142 is rotated relative to the housing 110.

Similar to the first iris 120 shown in FIG. 4, a medial portion of each arm of the second plurality of arms 144 of the second iris 140 may be configured to engage with medial portions of circumferentially adjacent arms of the second plurality of arms 144 to define the second central opening 146. The medial portion of each arm of the second plurality of arms 144 may include a second living hinge 145. In some embodiments, the second plurality of arms 144 may be integrally and/or monolithically formed with the second circumferential ring 142 from a single piece of material. In at least some embodiments, the first living hinge 143 and the second living hinge 145 of each arm of the second plurality of arms 144 may be configured to resiliently flex, deflect, and/or bend to permit relative movement between portions of each arm on opposite sides of the first living hinge 143 and/or the second living hinge 145. In a preferred configuration, the first iris 120 may be made from a polymeric material. Some suitable but non-limiting examples of materials that may be used to form the second iris 140, the second circumferential ring 142, the second plurality of arms 144, etc., including but not limited to metals and metal alloys, composites, ceramics, polymers, and the like, are described below.

In some embodiments, the second iris 140 may be manufactured using one or more a variety of methods. In some embodiments, the second iris 140 may be machined. In some embodiments, the second iris 140 may be cut using a waterjet. In some embodiments, the second iris 140 may be laser cut. In some embodiments, the second iris 140 may be injection molded. In some embodiments, the second iris 140 may be cast. Other methods of manufacture are also contemplated.

In some embodiments, as seen in FIG. 3 for example, the second iris 140 may include a second lever 141 fixedly attached to and/or extending radially outward from the second circumferential ring 142. In some embodiments, the second lever 141 may extend radially outward from the substantially circular outer perimeter of the second iris 140 and/or the second circumferential ring 142. In at least some embodiments, the second lever 141 may include a second cavity 147 formed therein. The second lever 141 may extend radially outward along a second radii extending outward from a center of the second central opening 146. Additionally, similar to the first iris 120 shown in FIG. 4, the second lever 141 may include a first side surface facing laterally from the second radii in a first direction and a second side surface disposed generally opposite the first side surface, the second side surface facing laterally from the second radii in a second direction generally opposite the first direction. In at least some embodiments, the second cavity 147 may be disposed between the first side surface and the second side surface of the second lever 141. In some embodiments, the second cavity 147 may be disposed radially between the first side surface and the second side surface of the second lever 141. In some embodiments, the second cavity 147 may be directly radially between the first side surface and the second side surface of the second lever 141. The purpose and/or use of the first side surface and/or the second side surface of the second lever 141 will be apparent.

In some embodiments, the projection 131 of the spacer plate 130 may include a second stop element (not visible) projecting axially and/or downward from a lower surface of the projection 131 and/or the spacer plate 130 opposite the first stop element 136. In some embodiments, the second stop element may be configured to engage and/or be received by the second cavity 147 of the second lever 141 of the second iris 140 to lock the second iris 140 and/or the second plurality of arms 144 in a first configuration. In at least some embodiments, the first configuration of the second iris 140 and/or the second plurality of arms 144 may be an open configuration or a radially expanded configuration. In the first configuration of the second iris 140 and/or the second plurality of arms 144, the second plurality of arms 144 and/or the medial portion of each arm of the second plurality of arms 144 may define a first size of the second central opening 146.

Figure 5:
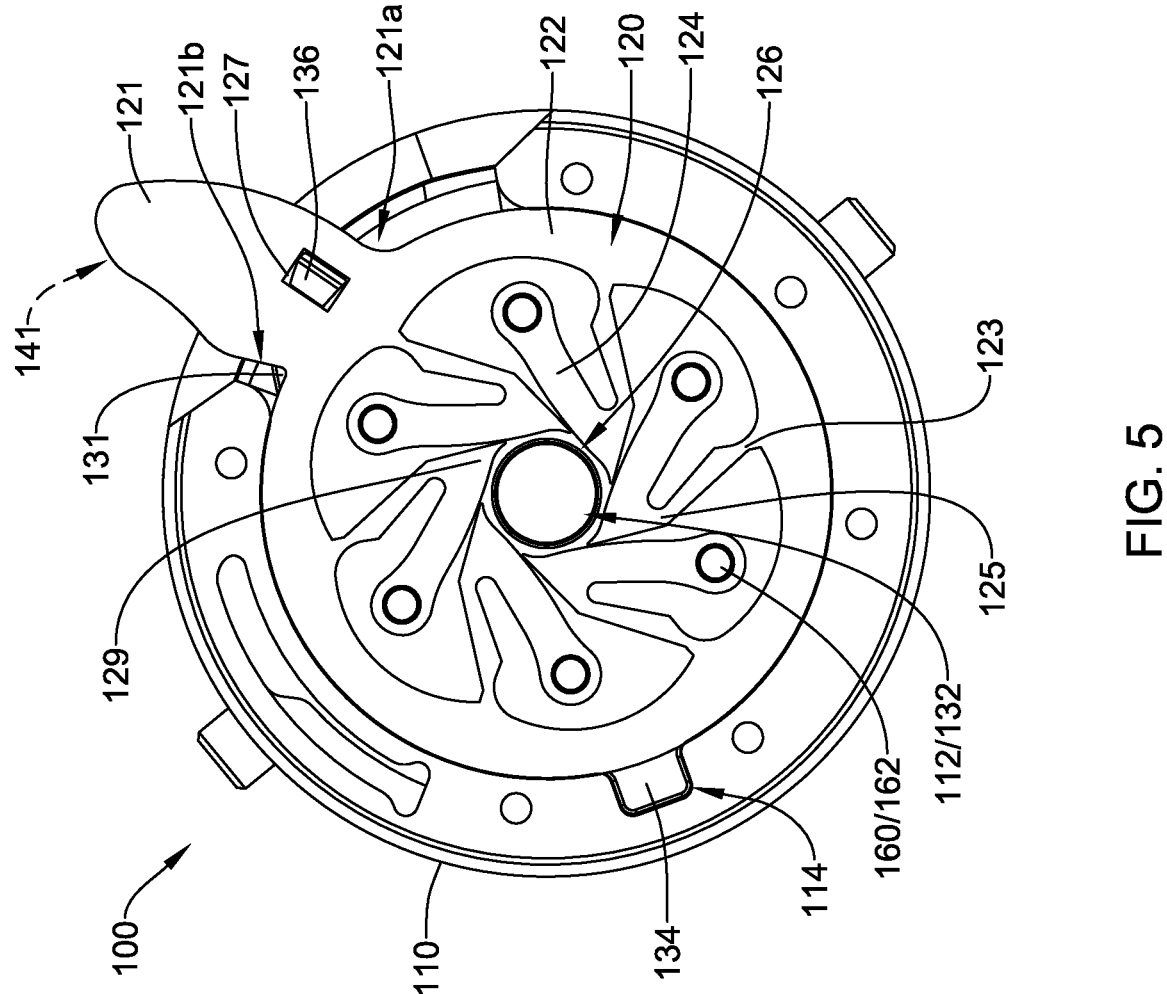
FIGS. 5-7 illustrate selected aspects related to the function of the device of FIGS. 1-4.
Figure 6:
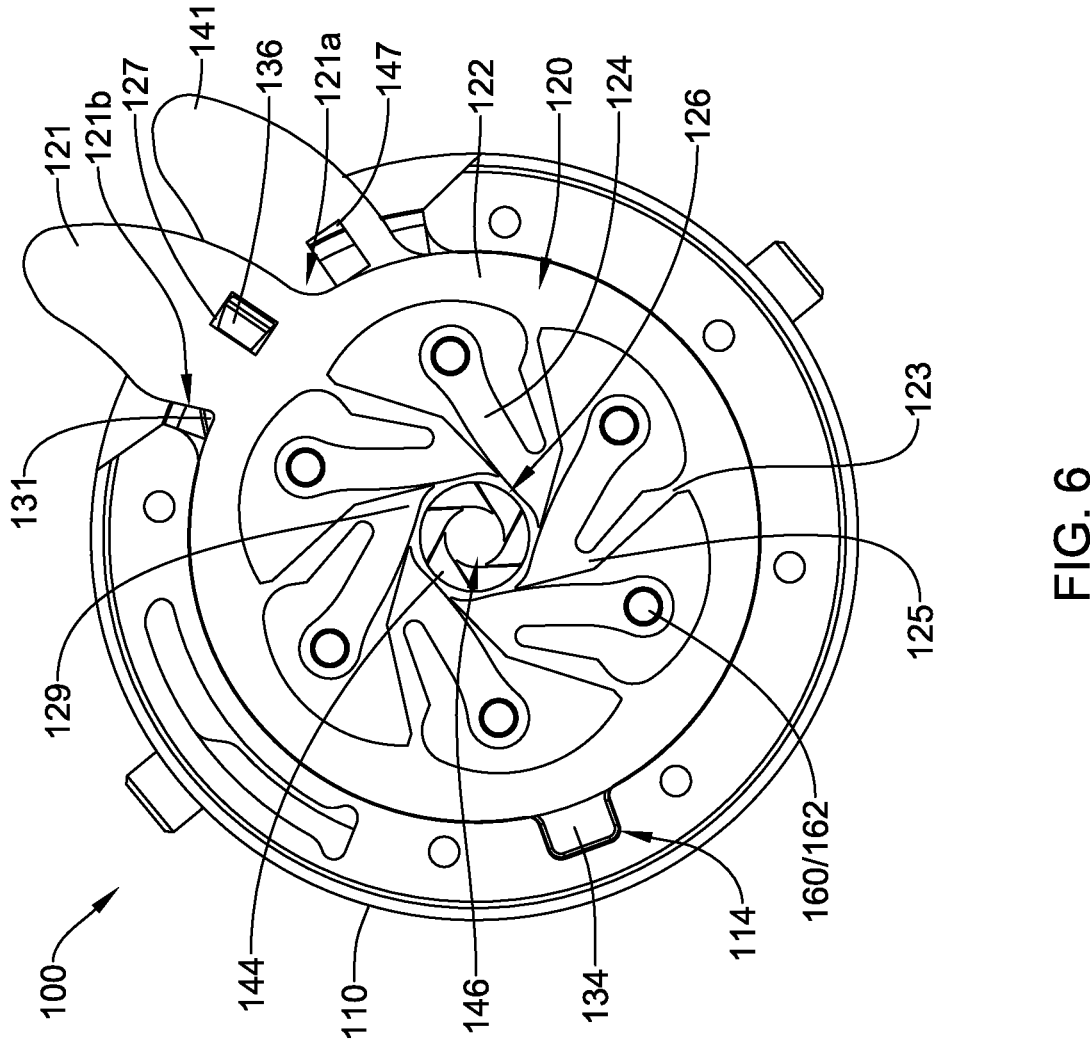
Figure 7:
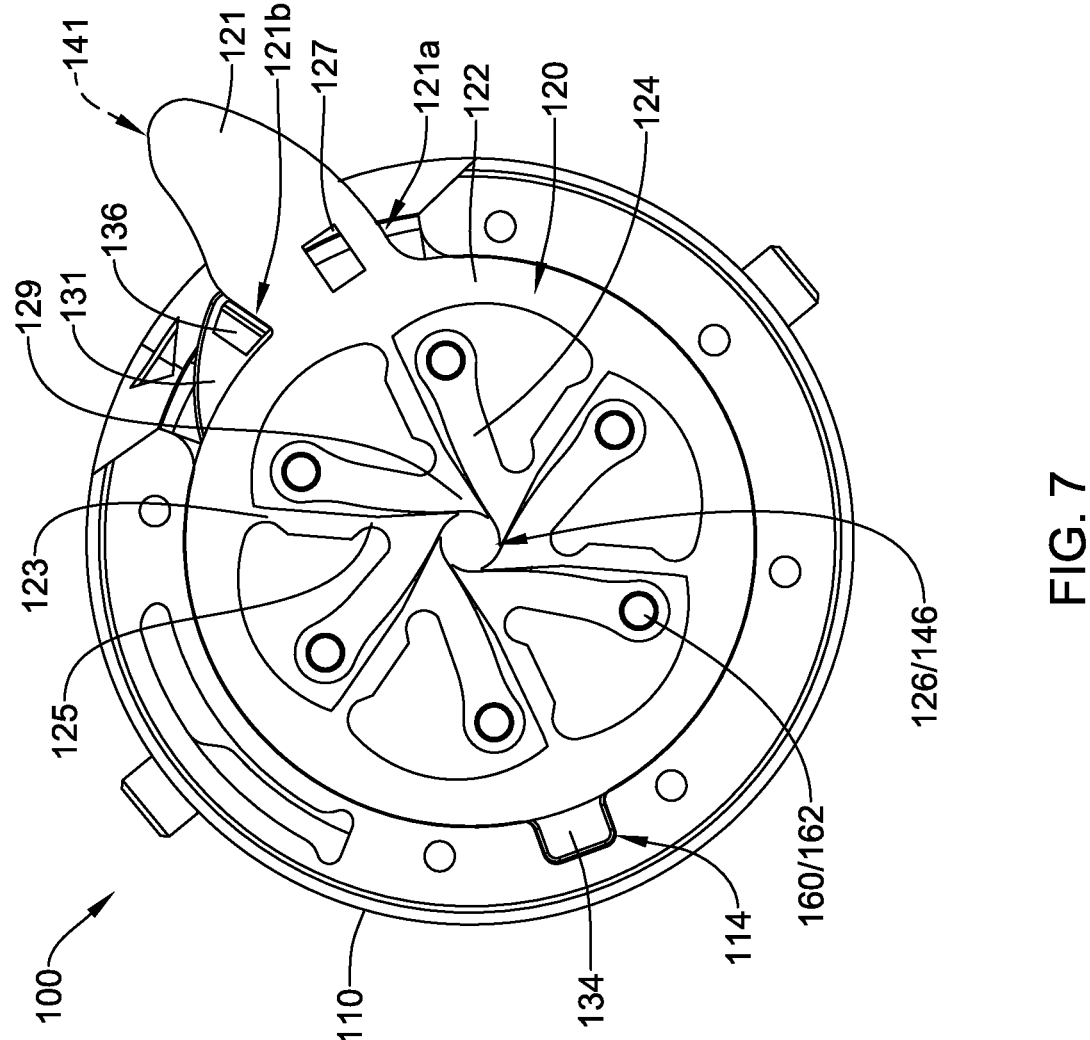

FIGS. 5-7 illustrate selected aspects related to the function and/or operation of the device 100. To improve clarity, the cover plate 150 is not shown. Each and every reference number illustrated may not be expressly discussed (and vice versa) with respect to FIGS. 5-7, but earlier discussion related to such reference numbers (e.g., with respect to FIGS. 1-4) may apply. In order to illustrate operation of the device 100, FIG. 5 will be compared to FIG. 7. FIG. 6 will be returned to momentarily.

FIG. 5 illustrates the first iris 120 and/or the first plurality of arms 124 in the first configuration. The first lever 121 may extend radially outward from the first circumferential ring 122 through a side opening in the housing 110. The first lever 121 may be movable and/or rotatable relative to the housing 110 within the side opening of the housing 110. The first cavity 127 of the first lever 121 of the first iris 120 is engaged with and/or receives the first stop element 136 of the projection 131 of the spacer plate 130 to lock the first iris 120 and/or the first plurality of arms 124 in the first configuration. The first plurality of arms 124 defines the first central opening 126. In the first configuration, the first plurality of arms 124 defines a first size of the first central opening 126. Similarly, while not expressly visible, the second iris 140 and/or the second plurality of arms 144 is also in the first configuration. The second lever 141 may extend radially outward from the second circumferential ring 142 through the side opening in the housing 110. The second lever 141 may be movable and/or rotatable relative to the housing 110 within the side opening of the housing. The second cavity 147 of the second lever 141 of the second iris 140 is engaged with and/or receives the second stop element of the projection 131 of the spacer plate 130 to lock the second iris 140 and/or the second plurality of arms 144 in the first configuration. The second plurality of arms 144 defines the second central opening 146. In the first configuration, the second central opening 146 has a first size.

Rotation of the first circumferential ring 122 of the first iris 120 relative to the housing 110 may change a size of the first central opening 126, as seen in FIG. 7. In at least some embodiments, the first plurality of arms 124 may be configured to shift between the first configuration and a second configuration via rotation of the first circumferential ring 122 relative to the housing 110. In some embodiments, rotation of the first circumferential ring 122 relative to the housing 110 may be achieved by shifting and/or rotating the first lever 121 relative to the housing 110. In some embodiments, the first plurality of arms 124 may be configured to shift between the first configuration and the second configuration via clockwise rotation of the first circumferential ring 122 and/or the first lever 121 relative to the housing 110, as may be seen when comparing FIG. 5 to FIG. 7. In the second configuration, the first plurality of arms 124 defines a second size of the first central opening 126 less than the first size. As may be seen in FIGS. 5 and 7, each arm of the first plurality of arms 124 may engage at least one other arm of the first plurality of arms 124 as the first plurality of arms 124 shifts from the first configuration to the second configuration. In some embodiments, the medial portion 129 of each arm of the first plurality of arms 124 may engage with the medial portion 129 of at least one other arm of the first plurality of arms 124 as the first plurality of arms 124 shifts from the first configurations to the second configuration to define the first central opening 126. In some embodiments, the medial portion 129 of each arm of the first plurality of arms 124 may engage with the medial portions of circumferentially and/or immediately adjacent arms of the first plurality of arms 124 as the first plurality of arms 124 shifts from the first configurations to the second configuration to define the first central opening 126.

As shown in FIG. 7, in the second configuration of the first iris 120 and/or the first plurality of arms 124, the second side surface 121B of the first lever 121 may engage and/or may contact a side surface of the first stop element 136 of the projection 131 to prevent counterclockwise rotation of the first lever 121 relative to the housing 110 (without deflecting one of the projection 131 or the first lever 121 away from the other), thereby locking the first iris 120 and/or the first plurality of arms 124 in the second configuration.

Returning to FIG. 6, rotation of the second circumferential ring 142 of the second iris 140 relative to the housing 110 may change a size of the second central opening 146. In at least some embodiments, the second plurality of arms 144 may be configured to shift between the first configuration and a second configuration via rotation of the second circumferential ring 142 relative to the housing 110. In some embodiments, rotation of the second circumferential ring 142 relative to the housing 110 may be achieved by shifting and/or rotating the second lever 141 relative to the housing 110. In some embodiments, the second plurality of arms 144 may be configured to shift between the first configuration and the second configuration via clockwise rotation of the second circumferential ring 142 and/or the second lever 141 relative to the housing 110, as may be seen when comparing FIG. 5 to FIG. 6. In the second configuration, the second plurality of arms 144 defines a second size of the second central opening 146 less than the first size. As may be seen in FIGS. 5 and 6, each arm of the second plurality of arms 144 may engage at least one other arm of the second plurality of arms 144 as the second plurality of arms 144 shifts from the first configuration to the second configuration. In some embodiments, the medial portion of each arm of the second plurality of arms 144 may engage with the medial portion of at least one other arm of the second plurality of arms 144 as the second plurality of arms 144 shifts from the first configuration to the second configuration to define the second central opening 146. In some embodiments, the medial portion of each arm of the second plurality of arms 144 may engage with the medial portions of circumferentially and/or immediately adjacent arms of the second plurality of arms 144 as the second plurality of arms 144 shifts from the first configuration to the second configuration to define the second central opening 146.

As may be inferred from FIG. 6, in the second configuration of the second iris 140 and/or the second plurality of arms 144, the second side surface of the second lever 141 may engage and/or may contact a side surface of the second stop element of the projection 131 to prevent counterclockwise rotation of the second lever 141 relative to the housing 110 (without deflecting one of the projection 131 or the second lever 141 away from the other), thereby locking the second iris 140 and/or the second plurality of arms 144 in the second configuration.

As shown in FIG. 6, the first iris 120, the first lever 121, and/or the first plurality of arms 124 may be moved, shifted, and/or actuated independently of the second iris 140, the second lever 141, and/or the second plurality of arms 144. As such, at some times and/or under some circumstances, the first central opening 126 may be at the first size while the second central opening 146 is at the second size, and vice versa.

In FIG. 7, both the first lever 121 of the first iris 120 and the second lever 141 of the second iris 140 have been rotated clockwise relative to the housing 110 to shift the first iris 120 and/or the first plurality of arms 124 and the second iris 140 and/or the second plurality of arms 144 to the second configuration. The first stop element 136 and the second stop element of the spacer plate 130 may function to prevent counterclockwise rotation of the first lever 121 and the second lever 141, respectively, to lock the first iris 120 and/or the first plurality of arms 124 and the second iris 140 and/or the second plurality of arms 144, respectively, in the second configuration.

Referring back to FIGS. 5 and 7 again, the movements and/or motions of the first plurality of arms 124 may be seen. As noted herein, in FIG. 5, the first plurality of arms 124 is in the first configuration. Clockwise rotation of the first lever 121 and/or the first circumferential ring 122 causes the end and/or the first living hinge 123 of each arm of the first plurality of arms 124 to shift in the clockwise direction as well. Since the second end of each arm of the first plurality of arms 124 is held in a fixed position relative to the housing 110 by the fastener 160 and/or the protrusion 162, the second end of each arm of the first plurality of arms 124 will pivot about the fastener 160 and/or the protrusion 162 as the first lever 121 and/or the first circumferential ring 122 is rotated. The first living hinge 123 and the second living hinge 125 of each arm of the first plurality of arms 124 may resiliently flex, deflect, and/or bend to facilitate a pivoting movement of the first plurality of arms 124. As the first lever 121 and/or the first circumferential ring 122 is rotated clockwise, each arm of the first plurality of arms 124 is prevent from rotation commensurately and/or equally around a central axis of the first central opening 126 due to the second end being fixed in position by the fastener 160 and/or the protrusion 162. Lengths of the various portions of each arm of the first plurality of arms 124 remain fixed and/or constant, wherein the first living hinge 123 and the second living hinge 125 cooperate with the various portions of each arm to form a linkage connecting the second end to the first circumferential ring 122. The first living hinge 123 and the second living hinge 125 of each arm of the first plurality of arms 124 may each form a hinge or a pivot point within each arm of the first plurality of arms 124.

Due to size (width, thickness, etc.), bulk, and/or stiffness, the portion of each arm connecting the second end of each arm to the medial portion 129 of each arm of the first plurality of arms 124 will remain substantially straight. As seen when comparing FIG. 5 to FIG. 7, as the first lever 121 and/or the first circumferential ring 122 is rotated clockwise, the medial portion 129 may shift radially inward relative to the first circumferential ring 122, thereby changing the size of the first central opening 126 defined by the first plurality of arms 124. In the first configuration shown in FIG. 5, the portion of each arm of the first plurality of arms 124 connected to the first circumferential ring 122 by the first living hinge 123 and/or extending between the first living hinge 123 and the second living hinge 125 may be oriented at an oblique angle to the first circumferential ring 122. As the first lever 121 and/or the first circumferential ring 122 is rotated clockwise toward the second configuration, the portion of each arm of the first plurality of arms 124 connected to the first circumferential ring 122 by the first living hinge 123 and/or extending between the first living hinge 123 and the second living hinge 125 may shift toward an angle that is closer to normal or perpendicular to the first circumferential ring 122, as seen in FIG. 7.

While not expressly visible in FIGS. 5 and 6, the movements and/or motions of the second plurality of arms 144 may be understood to be similar to or substantially the same as those of the first plurality of arms 124. By using living hinges to shift the irises and/or the pluralities of arms from the first configuration to the second configuration (and vice versa), the complexity and high part count of traditional stent compression devices may be reduced. As such, the cost of such devices may also be reduced. Additionally, in some embodiments, the device 100 may permit a stent to be loaded into a sheath without moving or advancing the stent through the device 100 multiple times, thereby reducing the number of steps required to sheath the stent, reducing or eliminating multiple compression steps, and/or reducing opportunity for damage to the stent. In some embodiments, the device 100 may be reusable following suitable sterilization techniques. In some embodiments, the device 100 may be disposable and/or may be classified or used as a single-use device.

Additionally, it is contemplated that the device 100 may include additional irises, intervening spacer plates, etc. to accommodate a stent of longer length and/or varying outer diameter (in a first configuration and/or in a compressed configuration). For example, in some embodiments, the second size of the first central opening 126 may be the same as the second size of the second central opening 146, and additional central openings of additional irises may have a second size that is the same as the second size of the first central opening 126 and/or the second central opening 146. In some embodiments, the second size of the first central opening 126 may be different from the second size of the second central opening 146, and additional central openings of additional irises may have a second size that is the same as the second size of the first central opening 126 and the second central opening 146, the additional central openings of additional irises may have a second size that is the same as the second size of one of the first central opening 126 and the second central opening 146, or the additional central openings of additional irises may have a second size that is the different from the second size of the first central opening 126 and the second central opening 146. Other configurations are also contemplated.

In some embodiments, the first iris 120 and/or the medial portions of the first plurality of arms 124, the second iris 140 and/or the medial portions of the second plurality of arms 144, and/or additional irises and/or medial portions of the pluralities of arms thereof could be shaped or tapered axially to accommodate stent having outer surfaces that are curved or tapered in an axial direction.

In some embodiments, the first iris 120 may have a first axial thickness and the second iris 140 may have a second axial thickness. In some embodiments, the first axial thickness may be equal to the second axial thickness. In some embodiments, the first axial thickness may be different from the second axial thickness. In some embodiments, the first axial thickness may be less than the second axial thickness. In some embodiments, the first axial thickness may be greater than the second axial thickness. In some embodiments, additional irises may each have an axial thickness. The axial thickness of any additional iris may be equal to, more than, or less than the first axial thickness and/or the second axial thickness, as desired, to accommodate stents having different sizes, different lengths, and/or different radial compression requirements along their length.

FIGS. 8-12 are cross-sectional views of the device 100 showing selected aspects of a method of radially compressing a stent. The device 100 may generally include elements and/or features as described herein. For improved clarity and understanding, some elements or features of the device 100 are not shown or are not shown in their entirety.

Figure 8:
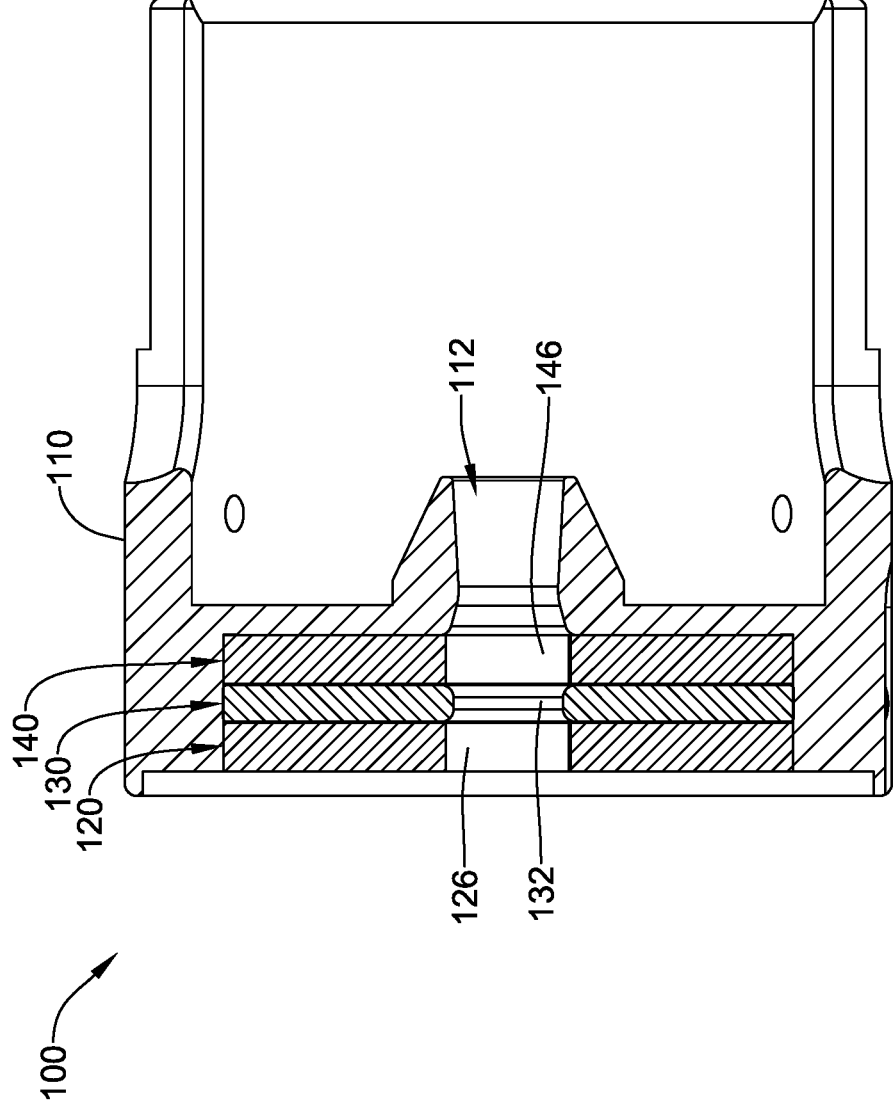
FIGS. 8-12 are partial cross-sectional views illustrating selected aspects of a method of radially compressing a stent using the device of FIGS. 1-7.

FIG. 8 illustrates a cross-sectional view of the device 100 for radially compressing a stent as described herein. The device 100 may include the housing 110 defining the central opening 112. In some embodiments, at least a portion of the central opening 112 may have an inner diameter that is tapered radially outward in an axial direction. In some embodiments, the central opening 112 may have an inner diameter that is generally constant. In some embodiments, the central opening 112 may have an inner diameter that is generally constant along a portion of its axial length and tapered along a different portion of its axial length. Other configurations are also contemplated.

The device 100 may include the first iris 120 including the first plurality of arms 124 (e.g., FIG. 3) defining the first central opening 126. The first central opening 126 may have a first size in a first configuration of the first plurality of arms 124 and a second size in a second configuration of the first plurality of arms 124. The device 100 may include the spacer plate 130 including and/or defining the central opening 132 therein. In at least some embodiments, the central opening 132 may have a generally fixed size. The device 100 may include the second iris 140 including the second plurality of arms 144 (e.g., FIG. 3) defining the second central opening 146. The second central opening 146 may have a first size in a first configuration of the second plurality of arms 144 and a second size in a second configuration of the second plurality of arms 144.

Figure 9:
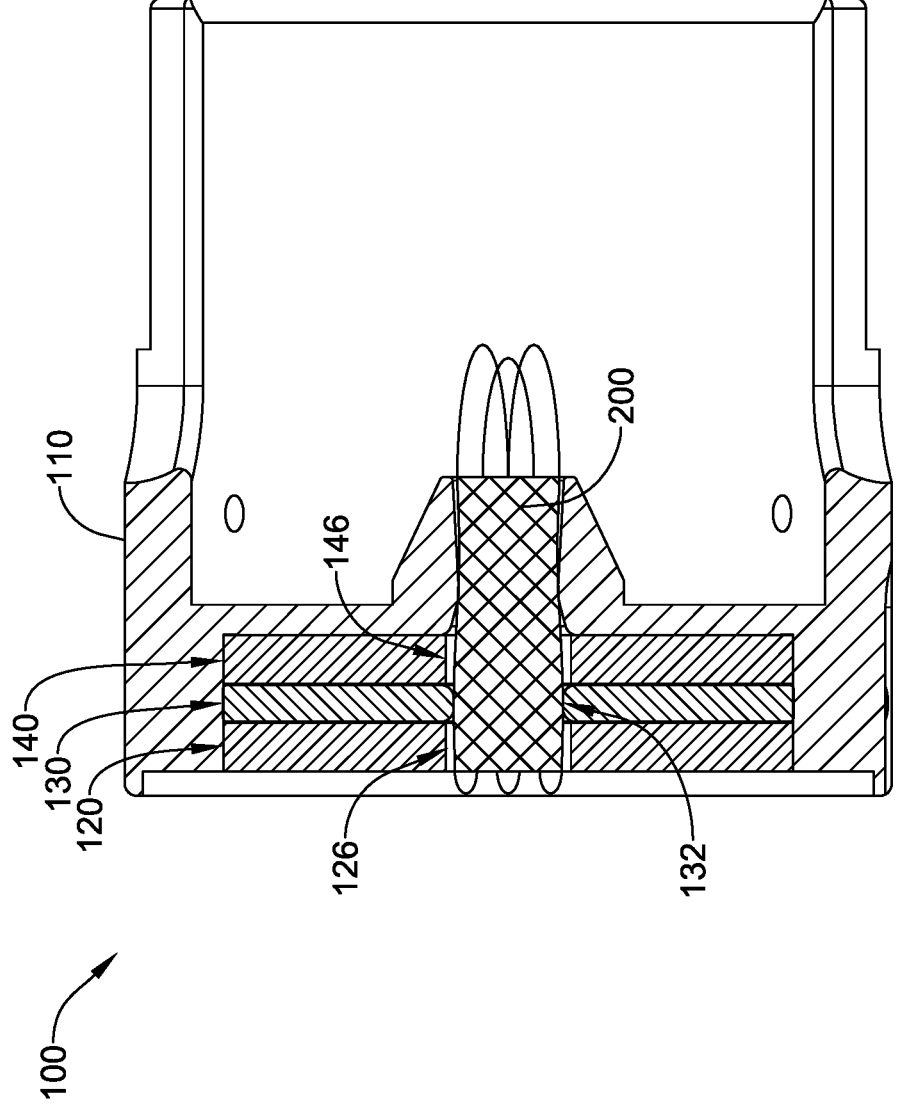

A method of radially compressing a stent may include inserting a stent 200 in a first configuration into the first central opening 126 of the first iris 120, as seen in FIG. 9.

In some embodiments, in the first configuration, the stent 200 may be in an expanded configuration. In some embodiments, in the first configuration, the stent 200 may be in a partially collapsed state. For example, in some embodiments, the device 100 may include a loading funnel (not shown) adapted to partially collapse the stent 200 as the stent 200 is inserted into the first central opening 126 of the first iris 120 and/or the central opening 112 of the housing 110. In some embodiments, the loading funnel may be configured to releasably attach to the housing 110. For example, in the view shown in FIG. 9, the loading funnel may be configured to be inserted into the housing 110 from the right side of the view until at least a portion of the loading funnel is positioned adjacent to and/or is engaged with the housing 110 proximate the central opening 112. In some embodiments, the method may include inserting the stent 200 into and/or through the central opening 112 of the housing 110 before inserting the stent 200 in the first configuration into first central opening 126 of the first iris 120.

In some embodiments, the method may include inserting the stent 200 in the first configuration into the second central opening 146 of the second iris 140 axially offset from the first iris 120. In some embodiments including the second iris 140, the method may include inserting the stent 200 in the first configuration into the central opening 132 of the spacer plate 130. Additionally, while not expressly illustrated, the method may include inserting the stent 200 into the cover plate opening 156 of the cover plate 150 (e.g., FIG. 3).

The stent 200 include an expandable framework defining a central lumen which, in some embodiments, may be substantially cylindrical. In some embodiments, the expandable framework may have a substantially circular cross-section. In some embodiments, the expandable framework can have a non-circular (e.g., D-shaped, elliptical, etc.) cross-section. In some embodiments, a non-circular expandable framework can be used to repair a mitral valve or another non-circular valve in the patient's heart or body. Some suitable but non-limiting examples of materials that may be used to form the expandable framework, including but not limited to metals and metal alloys, composites, ceramics, polymers, and the like, are described below.

The stent 200 and/or the expandable framework may be configured to shift from a collapsed configuration to an expanded configuration. In some embodiments, the expandable framework may be self-expanding. In some embodiments, the expandable framework may be self-biased toward the expanded configuration. In some embodiments, the expandable framework may be mechanically expandable. In some embodiments, the expandable framework may be balloon expandable. Other configurations are also contemplated.

In some embodiments, the stent 200 may be a part of a replacement heart valve implant. It will be appreciated that the replacement heart valve implant can be any type of heart valve (e.g., a mitral valve, an aortic valve, etc.). The replacement heart valve implant can be configured to allow one-way flow through the replacement heart valve implant from an inflow end to an outflow end. In some embodiments of a replacement heart valve implant, the stent 200 and/or the expandable framework may define a lower crown proximate an inflow end of the replacement heart valve implant, an upper crown proximate an outflow end of the replacement heart valve implant, and a plurality of stabilization arches extending downstream from the outflow end.

In some embodiments, the replacement heart valve implant may include a plurality of valve leaflets disposed within the central lumen. The plurality of valve leaflets may be coupled, secured, and/or fixedly attached to the stent 200 and/or the expandable framework. In some embodiments, the plurality of valve leaflets can be integrally formed with each other, such that the plurality of valve leaflets is formed as a single unitary and/or monolithic unit. In some embodiments, the plurality of valve leaflets may be formed integrally with other structures such as an inner skirt and/or an outer skirt, base structures, liners, or the like. The plurality of valve leaflets may be configured to substantially restrict fluid from flowing through the replacement heart valve implant in a closed position. For example, in some embodiments, free edges of the plurality of valve leaflets may move into coaptation with one another in the closed position to substantially restrict fluid from flowing through the replacement heart valve implant. The free edges of the plurality of valve leaflets may be move apart from each other in an open position to permit fluid flow through the replacement heart valve implant.

In some embodiments, the replacement heart valve implant may include an inner skirt. The inner skirt may be disposed on and/or extend along an inner surface of the stent 200 and/or the expandable framework. In at least some embodiments, the inner skirt may be fixedly attached to the stent 200 and/or the expandable framework. The inner skirt may direct fluid, such as blood, flowing through the replacement heart valve implant toward the plurality of valve leaflets. In at least some embodiments, the inner skirt may be fixedly attached to and/or integrally formed with the plurality of valve leaflets. The inner skirt may ensure the fluid flows through the central lumen and does not flow around the plurality of valve leaflets when they are in the closed position.

In some embodiments, the replacement heart valve implant may include an outer skirt. In some embodiments, the outer skirt may be disposed on and/or extend along an outer surface of the stent 200 and/or the expandable framework. In some embodiments, the outer skirt may be disposed between the stent 200 and/or the expandable framework and native tissue in order to prevent fluid, such as blood, flowing around the stent 200 and/or the expandable framework in a downstream direction so as to ensure that the plurality of valve leaflets can stop the flow of fluid when in the closed position.

In some embodiments, the plurality of valve leaflets may be comprised of a polymer, such as a thermoplastic polymer. In some embodiments, the plurality of valve leaflets may include at least 50 percent by weight of a polymer. In some embodiments, the plurality of valve leaflets may be formed from bovine pericardial or other living tissue. Other configurations and/or materials are also contemplated.

In some embodiments, the inner skirt and/or the outer skirt may include a polymer, such as a thermoplastic polymer. In some embodiments, the inner skirt and/or the outer skirt may include at least 50 percent by weight of a polymer. In some embodiments one or more of the plurality of valve leaflets, the inner skirt, and/or the outer skirt may be formed of the same polymer or polymers. In some embodiments, the polymer may be a polyurethane. In some embodiments, the inner skirt and/or the outer skirt may be substantially impervious to fluid. In some embodiments, the inner skirt and/or the outer skirt may be formed from a thin tissue (e.g., bovine pericardial, etc.). In some embodiments, the inner skirt and/or the outer skirt may be formed from a coated fabric material. In some embodiments, the inner skirt and/or the outer skirt may be formed from a nonporous and/or impermeable fabric material. Other configurations are also contemplated. Some suitable but non-limiting examples of materials that may be used to form the inner skirt and/or the outer skirt including but not limited to polymers, composites, and the like, are described below.

In some embodiments, the stent 200 and/or the replacement heart valve implant may have an outer extent of about 23 millimeters (mm), about 25 mm, about 27 mm, about 30 mm, etc. in an unconstrained configuration (e.g., in the expanded configuration). In some embodiments, the stent 200 and/or the replacement heart valve implant may have an outer extent of about 10 mm, about 9 mm about 8 mm, about 7 mm, about 6 mm, etc. in the collapsed configuration. Other configurations are also contemplated.

Figure 10:
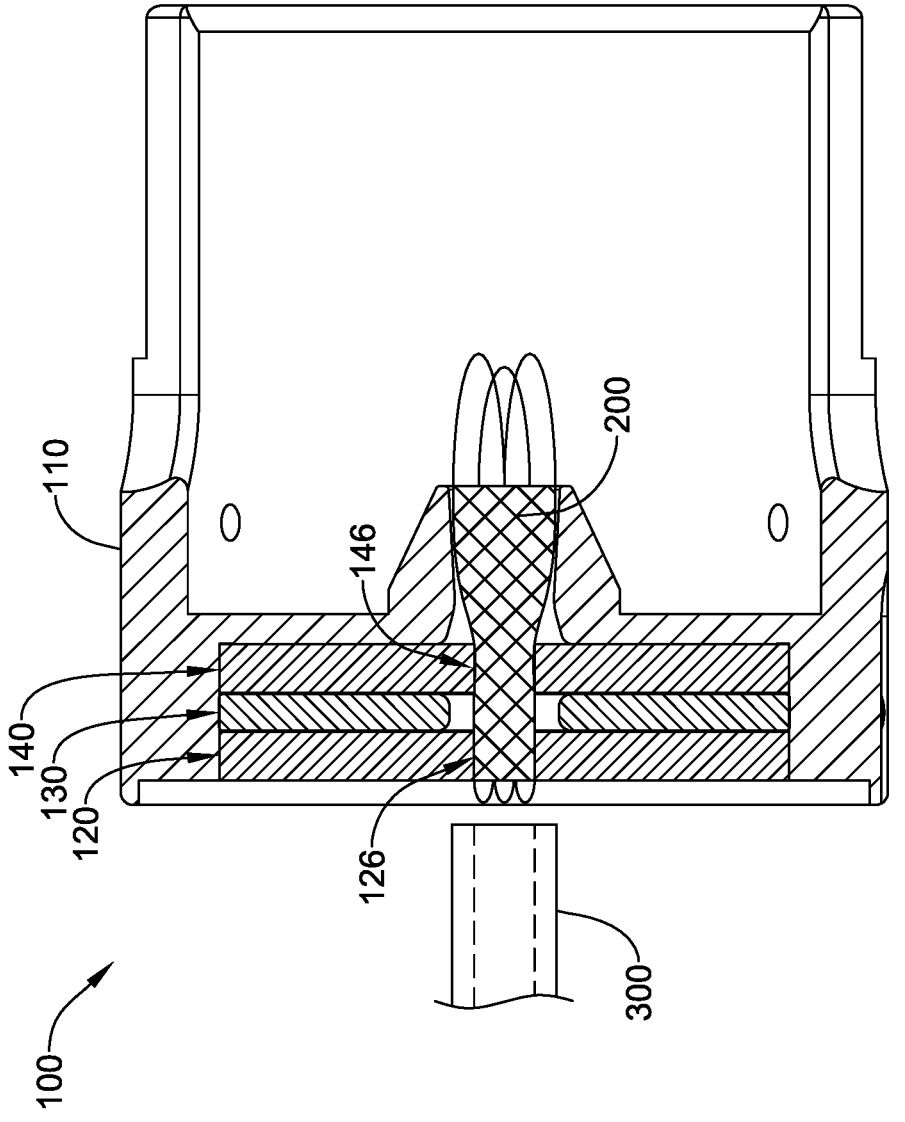

The method may include rotating the first circumferential ring 122 of the first iris 120 relative to the housing 110 disposed about the first circumferential ring 122 to shift the first plurality of arms 124 from the first configuration to the second configuration, as seen in FIG. 10, wherein the first central opening 126 has a first size in the first configuration (e.g., FIG. 9) and a second size in the second configuration less than the first size (e.g., FIG. 10). In some embodiments, the method may include rotating the first circumferential ring 122 of the first iris 120 clockwise relative to the housing 110 disposed about the first circumferential ring 122 to shift the first plurality of arms 124 from the first configuration to the second configuration. In the second configuration of the first plurality of arms 124, a first portion of the stent 200 disposed within the first iris 120 and/or the first central opening 126 may be in a radially compressed configuration. In some embodiments, the method may include rotating the second circumferential ring 142 of the second iris 140 relative to the housing 110 to shift the second plurality of arms 144 from a first configuration to a second configuration, wherein the second central opening 146 has a first size in the first configuration (e.g., FIG. 9) and a second size in the second configuration (e.g., FIG. 10) less than the first size. In some embodiments, the method may include rotating the second circumferential ring 142 of the second iris 140 clockwise relative to the housing 110 to shift the second plurality of arms 144 from a first configuration to a second configuration. In the second configuration of the second plurality of arms 144, a second portion of the stent 200 disposed within the second iris 140 and/or the second central opening 146 may be in the radially compressed configuration.

Figure 11:
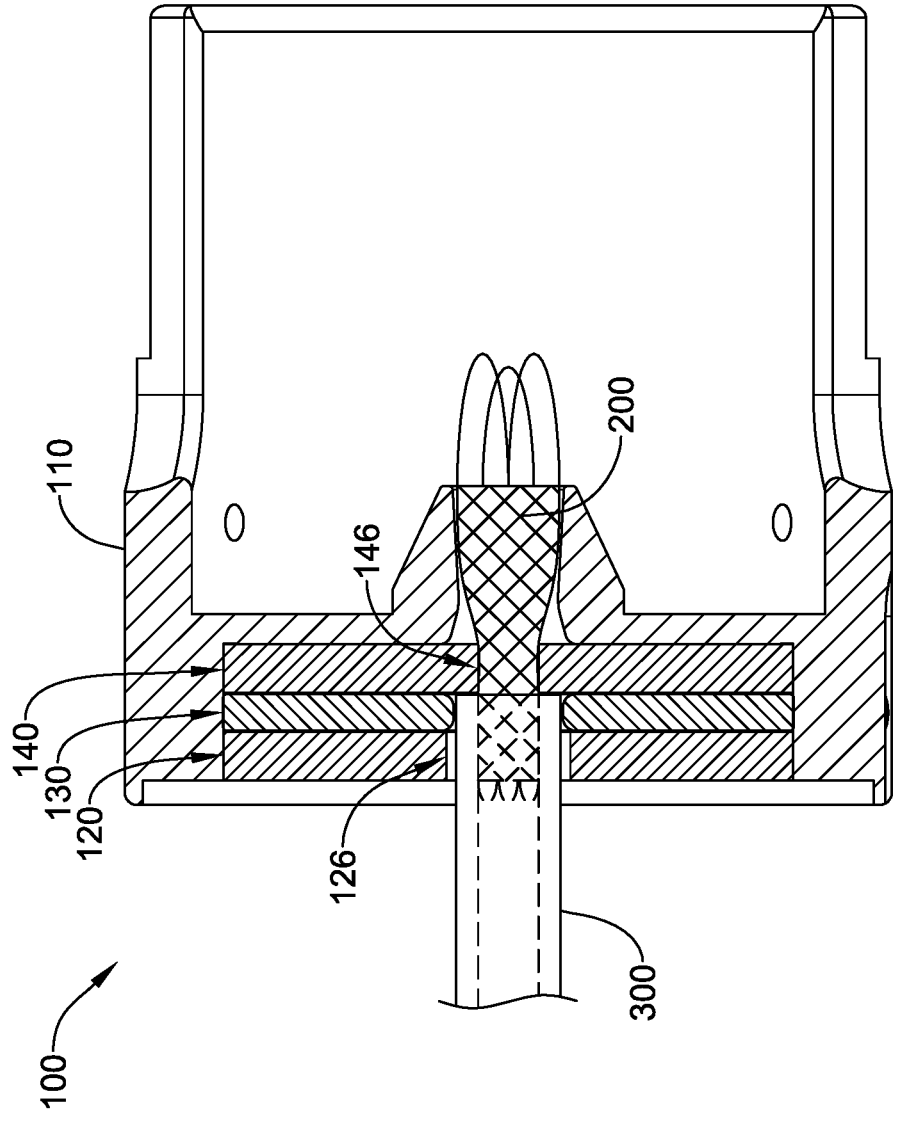

In some embodiments, the method may include positioning a sheath 300 proximate the first iris 120 with the first plurality of arms 124 in the second configuration and the first portion of the stent 200 disposed within the first iris 120 and/or the first central opening 126 in the radially compressed configuration, as seen in FIG. 10. After positioning the sheath 300 proximate the first iris 120, the method may include rotating the first circumferential ring 122 of the first iris 120 relative to the housing 110 to shift the first plurality of arms 124 from the second configuration to the first configuration. In some embodiments, the method may include rotating the first circumferential ring 122 of the first iris 120 counterclockwise relative to the housing 110 to shift the first plurality of arms 124 from the second configuration to the first configuration. The method may further include moving the sheath 300 into the first iris 120 over the stent 200 in the compressed configuration such that the first portion of the stent 200 that was disposed within the first iris 120 is disposed within a lumen of the sheath 300, as seen in FIG. 11. In some embodiments, the sheath 300 has an inner diameter less than an outer diameter of the stent 200 in the first configuration. As such, radial compression of the stent 200 is required in order to move the stent 200 into the lumen of the sheath 300.

Figure 12:
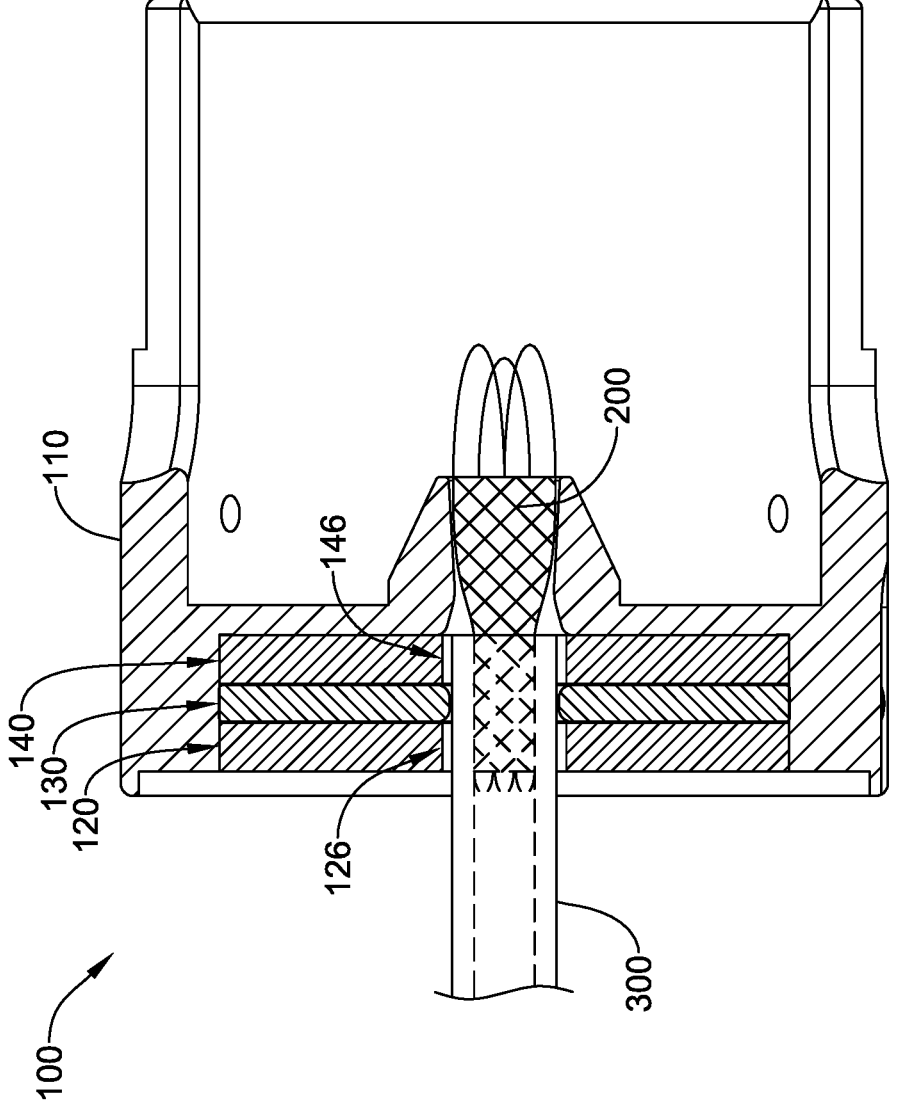

In some embodiments, after moving the sheath 300 into the first iris 120 over the stent 200, the method may further include rotating the second circumferential ring 142 of the second iris 140 relative to the housing 110 to shift the second plurality of arms 144 of the second iris 140 from the second configuration to the first configuration. In some embodiments, the method may include rotating the second circumferential ring 142 of the second iris 140 counterclockwise relative to the housing 110 to shift the second plurality of arms 144 of the second iris 140 from the second configuration to the first configuration. The method may further include moving the sheath 300 into the second iris 140 over the stent 200 in the compressed configuration such that the second portion of the stent 200 that was disposed within the second iris 140 is disposed within the lumen of the sheath 300, as seen in FIG. 12.

In some embodiments, wherein the device 100 includes additional irises, the process described above with respect to moving the sheath 300 into the first iris 120 and the second iris 140 may be repeated as necessary to move the sheath 300 over additional portions of the stent 200 disposed within those irises.

In some embodiments, if additional length of the stent 200 needs to be moved into the sheath 300, the stent 200 may be advanced through the central opening 112 of the housing 110 and the first iris 120 and the second iris 140 may be again shifted from the first configuration to the second configuration and the process may be repeated.

In some embodiments, after moving the sheath 300 into the second iris 140 over the stent 200 such that the second portion of the stent 200 that was disposed within the second iris 140 is disposed within the lumen of the sheath 300, the sheath 300 and the first and second portions of the stent 200 that were disposed within the first and second irises, respectively, may be advanced through the central opening 112 of the housing 110, and a separate sheath may be translated over an uncovered portion of the stent 200 toward the sheath 300 to cover at least some of the uncovered portion of the stent 200 that remains outside of the sheath 300. Other configurations are also contemplated.

Figure 13:
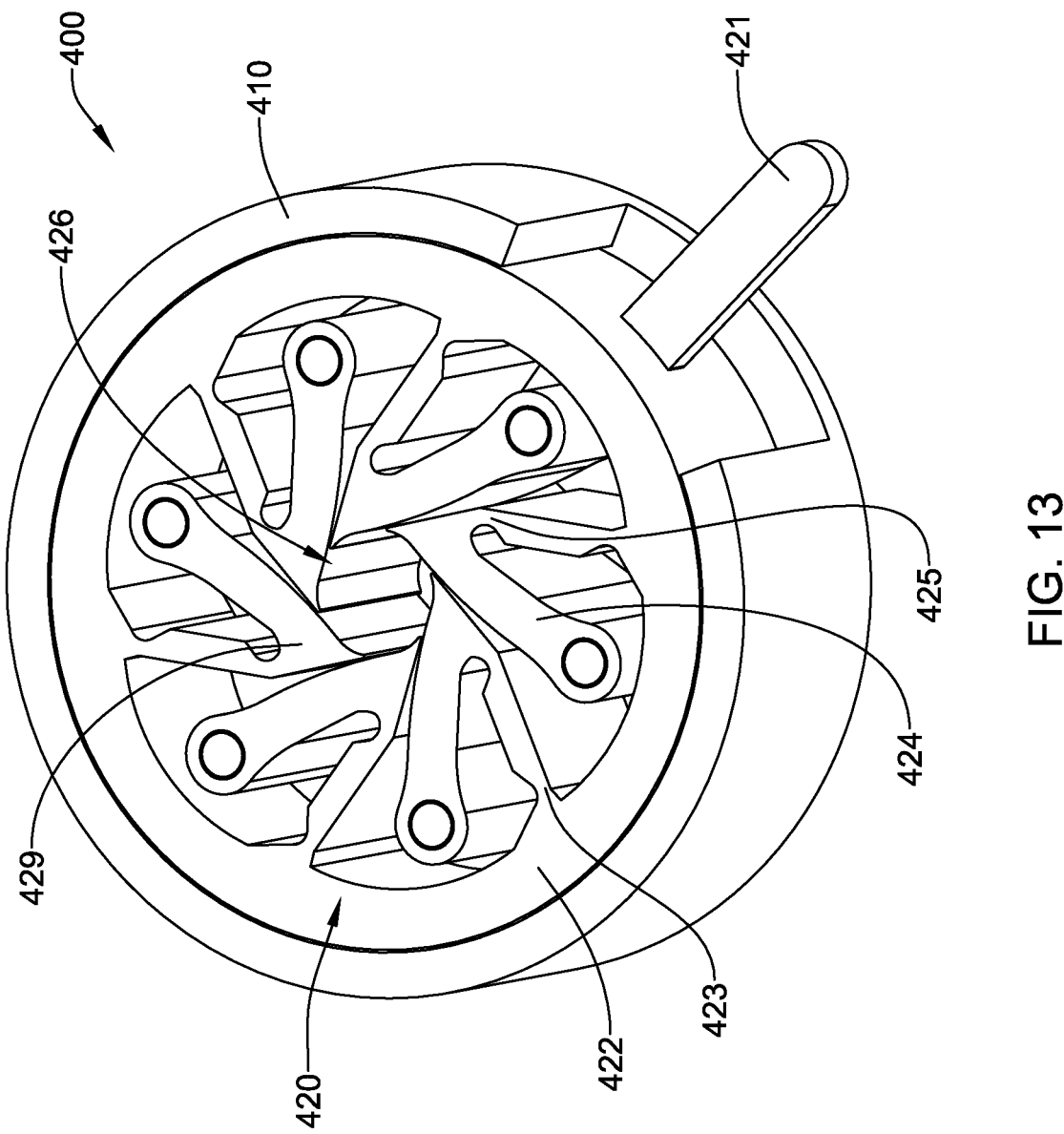
FIG. 13 illustrates selected aspects of an alternative configuration of the device for radially compressing a stent.

FIG. 13 illustrates an alternative configuration of a device 400 for radially compressing a stent. The device 400 may include a housing 410 including a central opening (not visible). In some embodiments, the device 400 may include a first iris 420 positioned adjacent the housing 410. In at least some embodiments, the first iris 420 may be positioned at least partially within the housing 410. In some embodiments, the device 400 may include a cover plate (not shown) positioned adjacent the housing 410. In some embodiments, the cover plate may be positioned at least partially within the housing 410.

In some embodiments, the cover plate may be removably secured to the housing 410. In some embodiments, the cover plate may be non-rotatable relative to the housing 410. In one example, the cover plate may be removably secured to the housing 410 using one or more fasteners. In another example, the cover plate and/or one or more protrusions extending from the cover plate may be configured to engage one or more slots or other features formed in the housing 410 to removably secure the cover plate to the housing 410. Other configurations are also contemplated.

In some embodiments, the first iris 420 may be movable with respect to the housing 410 and/or the cover plate. In some embodiments, at least a portion of the first iris 420 may be configured to rotate relative to the housing 410 and/or the cover plate.

In some embodiments, the device 400 may include a fastener engaged with the housing 410. In some embodiments, the fastener may be removable from and/or configured to be disengaged from the housing 410. The fastener may be configured to engage the first iris 420 and/or the cover plate. In some embodiments, the device 400 may include a plurality of fasteners engaged with the housing 410. In some embodiments, the plurality of fasteners may be removable from and/or configured to be disengaged from the housing 410. Other configurations are also contemplated.

In some embodiments, the device 400 may include a protrusion extending from the housing 410. In some embodiments, the protrusion may be fixedly attached to the housing 410. In some embodiments, the protrusion may be removable from and/or configured to be disengaged from the housing 410. The protrusion may be configured to engage the first iris 120 and/or the cover plate. In some embodiments, the device 400 may include a plurality of protrusions extending from the housing 410. In some embodiments, the plurality of protrusions may be fixedly attached to the housing 410. In some embodiments, the plurality of protrusions may be removable from and/or configured to be disengaged from the housing 410. Other configurations are also contemplated.

In some embodiments, the cover plate may include a cover plate opening. The cover plate opening may be aligned with and/or may be positioned coaxially relative to the central opening of the housing 410. In some embodiments, the cover plate may include a plurality of openings extending along a perimeter of the cover plate. The plurality of openings may be configured to receive fasteners therein to removably secure and/or attach the cover plate to the housing 410. The housing 410 may include a plurality of corresponding holes or recesses aligned with the plurality of openings in the cover plate and configured to receive the fasteners therein. In one example, the fasteners may be externally threaded screws or other threaded fasteners and the plurality of corresponding holes or recessed may include internal threads configured to threadably engage the externally threaded screws or other threaded fasteners. Other configurations and/or fastener types are also contemplated. Some suitable but non-limiting examples of materials that may be used to for the housing 410 and/or the cover plate, including but not limited to metals and metal alloys, composites, ceramics, polymers, and the like, are described below.

In some embodiments, the first iris 420 may include a first circumferential ring 422 positioned coaxially relative to the central opening of the housing 410. In some embodiments, the first circumferential ring 422 may be positioned adjacent the housing 410. In some embodiments, the first circumferential ring 422 may be positioned at least partially within the housing 410. In some embodiments, the first iris 420 and/or the first circumferential ring 422 may have a substantially circular outer perimeter.

The first iris 420 may include a first plurality of arms 424 extending radially inward from the first circumferential ring 422. The first plurality of arms 424 may define a first central opening 426 of the first iris 420. The first central opening 426 may be aligned with and/or may be positioned coaxially relative to the central opening of the housing 410.

A first end of each arm of the first plurality of arms 424 may be connected to the first circumferential ring 422 by a first living hinge 423 disposed between the first end and the first circumferential ring 422. In some embodiments, the first end of each arm of the first plurality of arms 424 may be directly connected to the first circumferential ring 422 by the first living hinge 423. In some embodiments, the first end of each arm of the first plurality of arms 424 may be fixedly attached to the first circumferential ring 422 by the first living hinge 423. In some embodiments, a second end of each arm of the first plurality of arms 424 may be secured relative to the housing 410. In some embodiments, the second end of each arm of the first plurality of arms 424 may include an aperture formed therein. In some embodiments, the fastener extends through the aperture and engages with the housing 410. In some embodiments, the aperture may be configured to engage with the protrusion extending from the housing 410. In at least some embodiments, the second end of each of the first plurality of arms 424 may be configured to rotate about the fastener and/or the protrusion when the first circumferential ring 422 is rotated relative to the housing 410.

In some embodiments, a medial portion 429 of each arm of the first plurality of arms 424 may be configured to engage with medial portions of circumferentially adjacent arms of the first plurality of arms 424 to define the first central opening 426. The medial portion 429 of each arm of the first plurality of arms 424 may include a second living hinge 425. In some embodiments, the first plurality of arms 424 may be integrally and/or monolithically formed with the first circumferential ring 422 from a single piece of material. In at least some embodiments, the first living hinge 423 and the second living hinge 425 of each arm of the first plurality of arms 424 may be configured to resiliently flex, deflect, and/or bend to permit relative movement between portions of each arm on opposite sides of the first living hinge 423 and/or the second living hinge 425. In a preferred configuration, the first iris 420 may be made from a polymeric material. Some suitable but non-limiting examples of materials that may be used to form the first iris 420, the first circumferential ring 422, the first plurality of arms 424, etc., including but not limited to metals and metal alloys, composites, ceramics, polymers, and the like, are described below.

In some embodiments, the first iris 420 may be manufactured using one or more a variety of methods. In some embodiments, the first iris 420 may be machined. In some embodiments, the first iris 420 may be cut using a waterjet. In some embodiments, the first iris 420 may be laser cut. In some embodiments, the first iris 420 may be injection molded. In some embodiments, the first iris 420 may be cast. Other methods of manufacture are also contemplated.

In some embodiments, the first iris 420 may include a first lever 421 fixedly attached to and/or extending radially outward from the first circumferential ring 422. In some embodiments, the first lever 421 may extend radially outward from the substantially circular outer perimeter of the first iris 420 and/or the first circumferential ring 422. The first lever 421 may extend radially outward along a first radii extending outward from a center of the first central opening 426.

In some embodiments, the first lever 421 may be configured to shift the first iris 420 and/or the first plurality of arms 424 between a first configuration and a second configuration. In at least some embodiments, the first configuration of the first iris 420 and/or the first plurality of arms 424 may be an open configuration or a radially expanded configuration. In the first configuration of the first iris 420 and/or the first plurality of arms 424, the first plurality of arms 424 and/or the medial portion 429 of each arm of the first plurality of arms 424 may define a first size of the first central opening 426.

The first lever 421 may extend radially outward from the first circumferential ring 422 through a side opening in the housing 410. The first lever 421 may be movable and/or rotatable relative to the housing 410 within the side opening of the housing 410.

Rotation of the first circumferential ring 422 of the first iris 420 relative to the housing 410 may change a size of the first central opening 426. In at least some embodiments, the first plurality of arms 424 may be configured to shift between the first configuration and a second configuration via rotation of the first circumferential ring 422 relative to the housing 410. In some embodiments, rotation of the first circumferential ring 422 relative to the housing 410 may be achieved by shifting and/or rotating the first lever 421 relative to the housing 410. In some embodiments, the first plurality of arms 424 may be configured to shift between the first configuration and the second configuration via clockwise rotation of the first circumferential ring 422 and/or the first lever 421 relative to the housing 410. In the second configuration, the first plurality of arms 424 defines a second size of the first central opening 426 less than the first size. Each arm of the first plurality of arms 424 may engage at least one other arm of the first plurality of arms 424 as the first plurality of arms 424 shifts from the first configuration to the second configuration. In some embodiments, the medial portion 429 of each arm of the first plurality of arms 424 may engage with the medial portion 429 of at least one other arm of the first plurality of arms 424 as the first plurality of arms 424 shifts from the first configuration to the second configuration to define the first central opening 426. In some embodiments, the medial portion 429 of each arm of the first plurality of arms 424 may engage with the medial portions of circumferentially and/or immediately adjacent arms of the first plurality of arms 424 as the first plurality of arms 424 shifts from the first configuration to the second configuration to define the first central opening 426.

In FIG. 13, the first lever 421 is disposed at an intermediate position within the side opening of the housing 410. As such, in the position shown in FIG. 13, the first iris 420 and/or the first plurality of arms 424 is disposed between the first configuration and a second configuration.

As discussed herein, clockwise rotation of the first lever 421 and/or the first circumferential ring 422 causes the end and/or the first living hinge 423 of each arm of the first plurality of arms 424 to shift in the clockwise direction as well. Since the second end of each arm of the first plurality of arms 424 is held in a fixed position relative to the housing 410 by the fastener and/or the protrusion, the second end of each arm of the first plurality of arms 424 will pivot about the fastener and/or the protrusion as the first lever 421 and/or the first circumferential ring 422 is rotated. The first living hinge 423 and the second living hinge 425 of each arm of the first plurality of arms 424 may resiliently flex, deflect, and/or bend to facilitate a pivoting movement of the first plurality of arms 424. As the first lever 421 and/or the first circumferential ring 422 is rotated clockwise, each arm of the first plurality of arms 424 is prevent from rotation commensurately and/or equally around a central axis of the first central opening 426 due to the second end being fixed in position by the fastener and/or the protrusion. Lengths of the various portions of each arm of the first plurality of arms 424 remain fixed and/or constant, wherein the first living hinge 423 and the second living hinge 425 cooperate with the various portions of each arm to form a linkage connecting the second end to the first circumferential ring 422. The first living hinge 423 and the second living hinge 425 of each arm of the first plurality of arms 424 may each form a hinge or a pivot point within each arm of the first plurality of arms 424.

Due to size (width, thickness, etc.), bulk, and/or stiffness, the portion of each arm connecting the second end of each arm to the medial portion 429 of each arm of the first plurality of arms 424 will remain substantially straight. In at least one configuration of the device 400, the first iris 420 may have a substantial thickness sufficient to and adapted to radially compress a stent, such as but not limited to a self-expanding stent, a balloon expandable stent, a self-expanding replacement heart valve implant, a balloon expandable replacement heart valve implant, etc., in a single step and/or motion. As the thickness of the first iris 420 increases, changes may be made to the width and/or thickness of the first living hinge 423 and/or the second living hinge 425 to permit the first iris 420 to function easily and smoothly without requiring excessing application of force to the first lever 421.

As the first lever 421 and/or the first circumferential ring 422 is rotated clockwise, the medial portion 429 may shift radially inward relative to the first circumferential ring 422, thereby changing the size of the first central opening 426 defined by the first plurality of arms 424. For example, the portion of each arm of the first plurality of arms 424 connected to the first circumferential ring 422 by the first living hinge 423 and/or extending between the first living hinge 423 and the second living hinge 425 may be oriented at an oblique angle to the first circumferential ring 422. As the first lever 421 and/or the first circumferential ring 422 is rotated clockwise toward the second configuration, the portion of each arm of the first plurality of arms 424 connected to the first circumferential ring 422 by the first living hinge 423 and/or extending between the first living hinge 423 and the second living hinge 425 may shift toward an angle that is closer to normal or perpendicular to the first circumferential ring 422.

By using living hinges to shift the first iris 420 and/or the first plurality of arms 424 from the first configuration to the second configuration (and vice versa), the complexity and high part count of traditional stent compression devices may be reduced. As such, the cost of such devices may also be reduced. Additionally, in some embodiments, the device 400 may permit a stent to be loaded into a sheath without moving or advancing the stent through the device 400 multiple times, thereby reducing the number of steps required to sheath the stent, reducing or eliminating multiple compression steps, and/or reducing opportunity for damage to the stent. In some embodiments, the device 400 may be reusable following suitable sterilization techniques. In some embodiments, the device 400 may be disposable and/or may be classified or used as a single-use device.

The materials that can be used for the various components of the device and the various elements thereof disclosed herein may include those commonly associated with medical devices and devices used and/or associated with medical devices. For simplicity purposes, the following discussion refers to the system. However, this is not intended to limit the devices and methods described herein, as the discussion may be applied to other elements, members, components, or devices disclosed herein, such as, but not limited to, the stent, the expandable framework, the first and/or second plurality of arms, the circumferential ring(s), the housing, etc. and/or elements or components thereof.

In some embodiments, the system and/or components thereof may be made from a metal, metal alloy, polymer (some examples of which are disclosed below), a metal-polymer composite, ceramics, combinations thereof, and the like, or other suitable material.

Some examples of suitable polymers may include poly-tetrafluoroethylene (PTFE), ethylene tetrafluoroethylene (ETFE), fluorinated ethylene propylene (FEP), polyoxym-ethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copo-lymers (for example, butylene/poly(alkylene ether) phtha-late and/or other polyester elastomers such as HYTREL® available from DuPont), polyamide (for example, DURE-THAN® available from Bayer or CRISTAMID® available from Elf Atochem), elastomeric polyamides, block poly-amide/ethers, polyether block amide (PEBA, for example available under the trade name PEBAX®), ethylene vinyl acetate copolymers (EVA), silicones, polyethylene (PE), MARLEX® high-density polyethylene, MARLEX® low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyethere-therketone (PEEK), polyimide (PI), polyetherimide (PEI), polyphenylene sulfide (PPS), polyphenylene oxide (PPO), poly paraphenylene terephthalamide (for example, KEV-LAR®), polysulfone, nylon, nylon-12 (such as GRIL-AMID® available from EMS American Grilon), perfluoro (propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, poly-isobutylene (PIB), polyisobutylene polyurethane (PIBU), polyurethane silicone copolymers (for example, Elast-Eon® from AorTech Biomaterials or ChronoSil® from Advan-Source Biomaterials), ionomers, biocompatible polymers, other suitable materials, or mixtures, combinations, copoly-mers thereof, polymer/metal composites, and the like. In some embodiments the sheath can be blended with a liquid crystal polymer (LCP). For example, the mixture can con-tain up to about 6 percent LCP.

Some examples of suitable metals and metal alloys include stainless steel, such as 304V, 304L, and 316LV stainless steel; mild steel; nickel-titanium alloy such as linear elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTEL-LOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-N® and the like), nickel-molybde-num alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; platinum; palladium; gold; combinations thereof; or any other suitable material. It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed is:

1. A device for radially compressing a stent, comprising:
a housing including a central opening; and
a first iris positioned adjacent the housing;
wherein the first iris includes a first circumferential ring positioned coaxially relative to the central opening and a first plurality of arms extending radially inward from the first circumferential ring;
wherein the first plurality of arms is monolithically formed with the first circumferential ring from a single piece of material;
wherein the first plurality of arms defines a first central opening positioned coaxially relative to the central opening of the housing;
wherein rotation of the first circumferential ring relative to the housing changes a size of the first central opening.

2. The device of claim 1, wherein a first end of each arm of the first plurality of arms is connected to the first circumferential ring by a first living hinge disposed between the first end and the first circumferential ring.

3. The device of claim 1, wherein a second end of each arm of the first plurality of arms is secured relative to the housing.

4. The device of claim 3, wherein the second end of each arm of the first plurality of arms includes an aperture formed therein.

5. The device of claim 4, wherein a fastener extends through the aperture and engages with the housing.

6. The device of claim 4, wherein the aperture is config-ured to engage with a protrusion extending from the hous-ing.

7. The device of claim 1, wherein a medial portion of each arm of the first plurality of arms is configured to engage with medial portions of circumferentially adjacent arms of the first plurality of arms to define the first central opening.

8. The device of claim 7, wherein the medial portion of each arm includes a second living hinge.

9. A device for radially compressing a stent, comprising:
a housing including a central opening; and
a first iris positioned adjacent the housing;
wherein the first iris includes a first circumferential ring positioned coaxially relative to the central opening of the housing and a first plurality of arms extending radially inward from the first circumferential ring;
wherein the first plurality of arms is monolithically formed with the first circumferential ring from a single piece of material;
wherein the first plurality of arms defines a first central opening positioned coaxially relative to the central opening of the housing;
wherein the first plurality of arms is configured to shift between a first configuration and a second configura-tion via rotation of the first circumferential ring relative to the housing.

10. The device of claim 9, wherein in the first configu-ration, the first plurality of arms defines a first size of the first central opening, and in the second configuration, the first plurality of arms defines a second size of the first central opening less than the first size.

11. The device of claim 9, wherein each arm of the first plurality of arms engages at least one other arm of the first plurality of arms as the first plurality of arms shifts from the first configuration to the second configuration.

12. The device of claim 9, wherein a first end of each arm of the first plurality of arms is fixedly attached to the first circumferential ring by a first living hinge.

13. The device of claim 9, further comprising a second iris axially offset from the first iris;

wherein the second iris includes a second circumferential ring positioned coaxially relative to the central opening of the housing and a second plurality of arms extending radially inward from the second circumferential ring;

wherein the second plurality of arms defines a second central opening positioned coaxially relative to the central opening of the housing;

wherein the second plurality of arms is configured to shift between a first configuration and a second configuration via rotation of the second circumferential ring relative to the housing.

14. A method of radially compressing a stent, comprising:

inserting a stent in a first configuration into a first iris, wherein the first iris includes a first circumferential ring and a first plurality of arms extending radially inward from the first circumferential ring to define a first central opening, wherein the first plurality of arms is monolithically formed with the first circumferential ring from a single piece of material; and rotating the first circumferential ring relative to a housing disposed about the first circumferential ring to shift the first plurality of arms from a first configuration to a second configuration, wherein the first central opening has a first size in the first configuration and a second size in the second configuration less than the first size;

wherein in the second configuration of the first plurality of arms, a first portion of the stent disposed within the first iris is in a radially compressed configuration.

15. The method of claim 14, further comprising:

positioning a sheath proximate the first iris with the first plurality of arms in the second configuration and the first portion of the stent disposed within the first iris in the radially compressed configuration;

rotating the first circumferential ring relative to the housing to shift the first plurality of arms from the second configuration to the first configuration; and moving the sheath into the first iris over the stent such that the first portion of the stent that was disposed within the first iris is disposed within the sheath.

16. The method of claim 15, wherein the sheath has an inner diameter less than an outer diameter of the stent in the first configuration.

17. The method of claim 14, wherein inserting the stent further includes inserting the stent in the first configuration into the first iris and a second iris axially offset from the first iris, wherein the second iris includes a second circumferential ring and a second plurality of arms extending radially inward from the second circumferential ring to define a second central opening.

18. The method of claim 17, further comprising:

rotating the second circumferential ring relative to the housing to shift the second plurality of arms from a first configuration to a second configuration, wherein the second central opening has a first size in the first configuration and a second size in the second configuration less than the first size;

wherein in the second configuration of the second plurality of arms, a second portion of the stent disposed within the second iris is in the radially compressed configuration.

19. The method of claim 18, further comprising:

positioning a sheath proximate the first iris with the first plurality of arms in the second configuration and the first portion of the stent disposed within the first iris in the radially compressed configuration;

rotating the first circumferential ring relative to the housing to shift the first plurality of arms from the second configuration to the first configuration;

moving the sheath into the first iris over the stent such that the first portion of the stent that was disposed within the first iris is disposed within the sheath;

rotating the second circumferential ring relative to the housing to shift the second plurality of arms from the second configuration to the first configuration; and moving the sheath into the second iris over the stent such that the second portion of the stent that was disposed within the second iris is disposed within the sheath.

* * * * *